United States Patent
Haines et al.

[11] Patent Number: 6,056,754
[45] Date of Patent: *May 2, 2000

[54] METHOD AND APPARATUS FOR PATELLA RESECTION AND GUIDE HANDLE

[75] Inventors: Timothy G. Haines, Stillwater, Minn.; David B. Goldstein, Weehawken, N.J.

[73] Assignee: Hudson Surgical Design, Inc., Weehawken, N.J.

[*] Notice: This patent is subject to a terminal disclaimer.

[21] Appl. No.: 09/156,161

[22] Filed: Sep. 17, 1998

Related U.S. Application Data

[63] Continuation of application No. 08/603,582, Feb. 20, 1996, Pat. No. 5,810,827, which is a continuation-in-part of application No. 08/300,379, Sep. 2, 1994, Pat. No. 5,514,139, and a continuation-in-part of application No. 08/342,143, Nov. 18, 1994, Pat. No. 5,597,379, which is a continuation-in-part of application No. 08/300,379, and a continuation-in-part of application No. 08/479,363, Jun. 7, 1995, Pat. No. 5,643,272, which is a continuation-in-part of application No. 08/300,379, and a continuation-in-part of application No. 08/342,143, which is a continuation-in-part of application No. 08/300,379.

[51] Int. Cl.⁷ ..................................................... A61B 17/56
[52] U.S. Cl. .................................................. 606/80; 606/88
[58] Field of Search ................................ 606/88, 87, 86, 606/96, 98, 79, 80, 81, 82

[56] References Cited

U.S. PATENT DOCUMENTS

| | | |
|---|---|---|
| 4,457,307 | 7/1984 | Stillwell . |
| 4,474,177 | 10/1984 | Whiteside . |
| 4,487,203 | 12/1984 | Androphy . |
| 4,566,448 | 1/1986 | Rohr, Jr. . |
| 4,586,496 | 5/1986 | Keller . |
| 4,653,488 | 3/1987 | Kenna . |
| 4,721,104 | 1/1988 | Kaufman et al. . |
| 4,722,330 | 2/1988 | Russell et al. . |
| 4,736,737 | 4/1988 | Fargie et al. . |
| 4,787,383 | 11/1988 | Kenna . |
| 4,892,093 | 1/1990 | Zarnowski et al. . |
| 4,896,663 | 1/1990 | Vandewalls . |
| 5,002,545 | 3/1991 | Whiteside et al. . |
| 5,047,032 | 9/1991 | Jellicoe . |
| 5,049,149 | 9/1991 | Schmidt . |
| 5,053,037 | 10/1991 | Lackey . |
| 5,098,436 | 3/1992 | Ferrante et al. . |
| 5,100,409 | 3/1992 | Coates et al. . |
| 5,129,909 | 7/1992 | Sutherland . |
| 5,147,365 | 9/1992 | Whitlock et al. . |
| 5,228,459 | 7/1993 | Caspari et al. . |
| 5,234,432 | 8/1993 | Brown . |
| 5,250,050 | 10/1993 | Poggie et al. . |
| 5,263,498 | 11/1993 | Caspari et al. . |
| 5,269,786 | 12/1993 | Morgan . |
| 5,284,482 | 2/1994 | Mikhail . |
| 5,304,181 | 4/1994 | Caspari et al. . |
| 5,306,276 | 4/1994 | Johnson et al. . |
| 5,342,368 | 8/1994 | Peterson . |
| 5,542,947 | 8/1996 | Treacy . |

*Primary Examiner*—Gary Jackson
*Assistant Examiner*—David O. Reip
*Attorney, Agent, or Firm*—Wolff & Samson

[57] ABSTRACT

A method and apparatus is provided for cutting bone. In one embodiment, a femur is resected by means of pattern plates having a cutting path with at least two continuous, non-coplanar guide surfaces. The cutting path has a similar profile to the interior profile of a femoral prosthesis. The cutting path guides a reciprocating, oscillating, or rotating cutting tool along a path for removing material from some or all of the distal femur to accept a distal femoral prosthesis. The cutting tool can be a cylindrical milling bit, and can even have a curvilinear profile to cut bone such that it has a three dimensional profile in cross section. Pattern plates can also be used to cut or remove material from other bones.

15 Claims, 22 Drawing Sheets

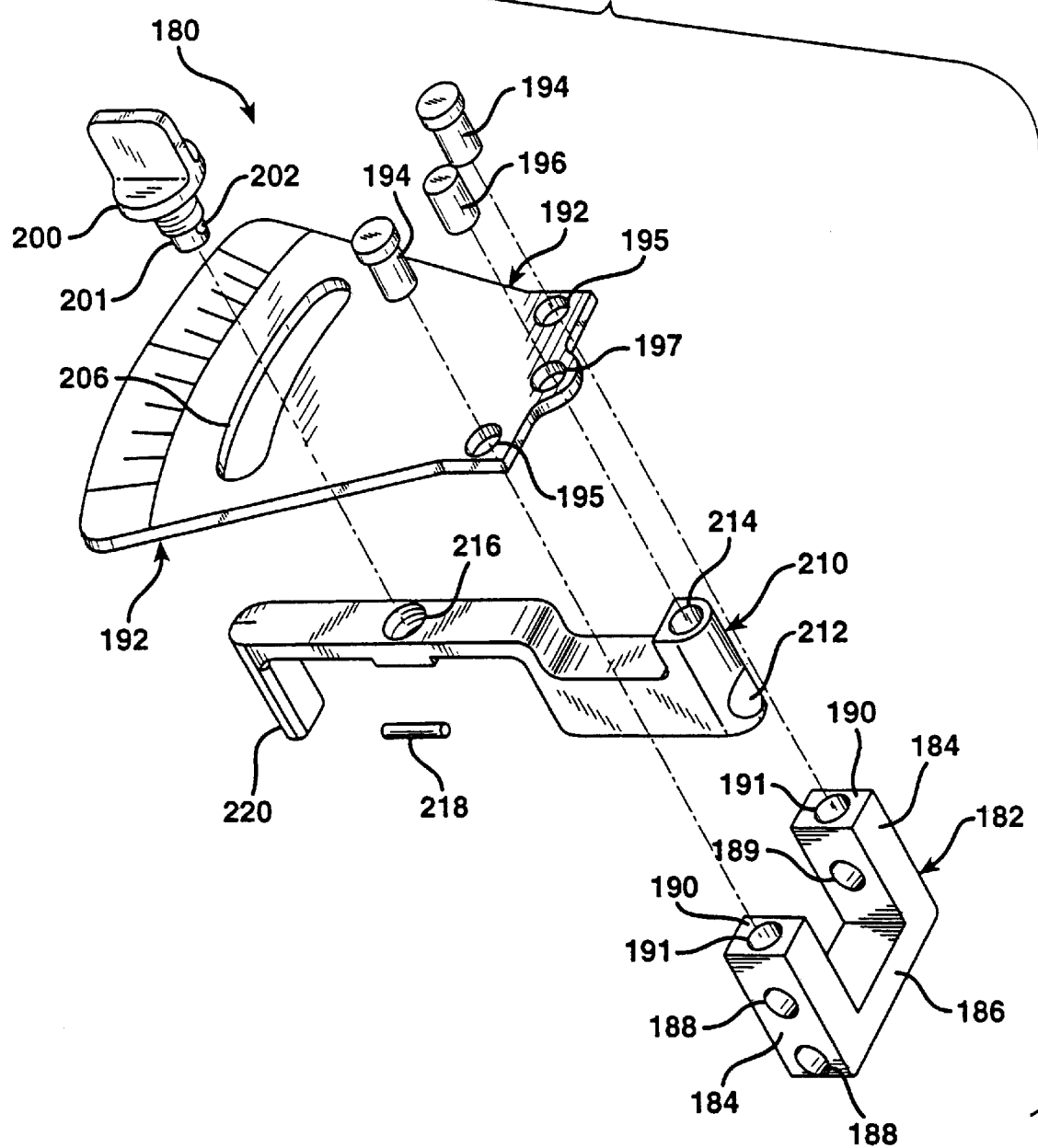

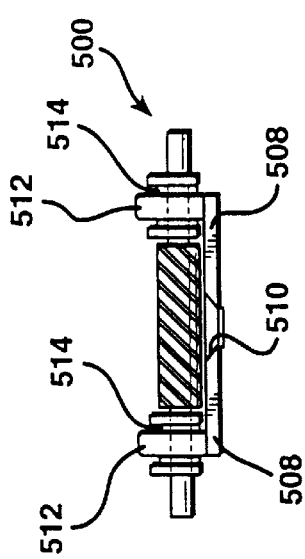
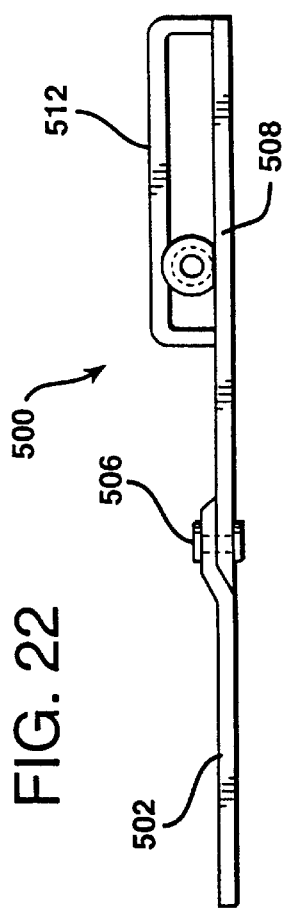
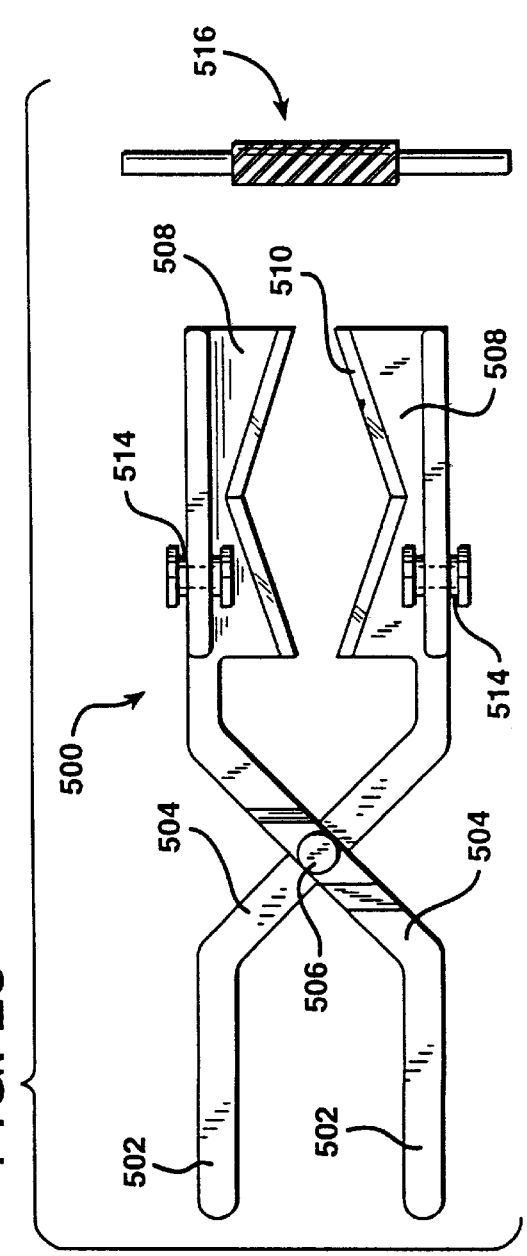

METHOD AND APPARATUS FOR PATELLA RESECTION AND GUIDE HANDLE

RELATED APPLICATIONS

This application is a continuation of application Ser. No. 08/603,582, filed Feb. 20, 1996, now U.S. Pat. No. 5,810,827, which is:

a continuation-in-part of application Ser. No. 08/300,379, filed Sep. 2, 1994, now U.S. Pat. No. 5,514,139; and a continuation-in-part of application Ser. No. 08/342,143, filed Nov. 18, 1994, now U.S. Pat. No. 5,597,379, which is a continuation-in-part of application Ser. No. 08/300,379, filed Sep. 2, 1994, now U.S. Pat. No. 5,514,139; and a continuation-in-part of application Ser. No. 08/479,363, filed Jun. 7, 1995, now U.S. Pat. No. 5,643,272, which is a continuation-in-part of application Ser. No. 08/300,379, filed Sep. 2, 1994, now U.S. Pat. No. 5,514,139 and a continuation-in-part of application Ser. No. 08/342,143, filed Nov. 18, 1994, now U.S. Pat. No. 5,597,379, which is a continuation-in-part of application Ser. No. 08/300,379, filed Sep. 2, 1994, now U.S. Pat. No. 5,514,139.

The entire disclosures of these related applications are expressly incorporated herein by reference.

BACKGROUND OF THE INVENTION

1. Field of the Invention

This invention generally relates to a method and apparatus for removing material from bone to create specifically shaped surfaces on or in bone. These surfaces may allow for the interconnection or attachment of various prosthetic devices, allograft or autograft material, or other objects either indigenous or foreign to the body.

2. Related Art

Many of the specific applications of the method and apparatus of the present invention as described herein apply to Total Knee Replacement, a surgical procedure wherein planar surfaces and/or curvilinear surfaces must be created in or on bone to allow for proper attachment or implantation of prosthetic devices. However, it should be noted that it is within the scope of the present invention to apply the methods and apparatus herein described to the removal of any kind of material from bones in any other application where it is necessary, desirable or useful to remove such material from bones.

Different methods and apparatus have been developed in the past to enable a surgeon to remove bony material to create specifically shaped surfaces in or on a bone for various reasons including to allow for attachment of various devices or objects to the bone. Keeping in mind that the ultimate goal of any surgical procedure is to restore the body to normal function, it is critical that the quality and orientation of the cut, as well as the quality of fixation, and the location and orientation of objects or devices attached to the bone, is sufficient to ensure proper healing of the body, as well as appropriate mechanical function of the musculoskeletal structure.

In Total Knee Replacement a series of planar and/or curvilinear surfaces, or "resections," are created to allow for the attachment of prosthetic or other devices to the femur, tibia and/or patella. In the case of the femur, it is common to use the central axis of the femur, the posterior and distal femoral condyles, and/or the anterior distal femoral cortex as guides to determine the location and orientation of distal femoral resections. The location and orientation of these resections are critical in that they dictate the final location and orientation of the distal femoral implant. It is commonly thought that the location and orientation of the distal femoral implant are critical factors in the success or failure of the artificial knee joint. Past efforts have not been successful in consistently and/or properly locating and orienting distal femoral resections.

Such previous efforts at femoral resections are set forth in the following patents, none of which teach or suggest all of the benefits and advantages of the present invention. These previous patents include:

Stillwell, U.S. Pat. No. 4,457,307, which discloses a movable saw and saw carriage which may be mounted to a patient's femur and positioned to cut the femur bone. An elongated rail is secured substantially parallel to the femur. A saw carriage and a carriage housing are attached to the rail. The saw has a blade extending substantially parallel to the direction of linear movement of the saw carriage. The saw carriage is slidably guided along paths substantially parallel to the elongated rails for making cuts in the femur bone. The saw may be positioned in a plurality of second positions where the saw carriage is slidably guided in paths substantially perpendicular to the elongated rail for making traverse distal femur cuts and for scoring the tibia cortex. Additionally, the saw may be positioned in a plurality of third positions where the saw carriage is slidably guided to form an acute angle with elongated rail for making anterior and posterior femur chamfer cuts.

Androphy, U.S. Pat. No. 4,487,203, discloses a knee resection system comprising a guide member, femur and tibia guide rods, a tibia adaptor, a tibia bar, and a femur bar. After the distal femoral condyles are resected, the guide member is attached to the tibia guide rod extending into the tibia. The tibia guide rod has a second guide at a right angle for receiving the guide member. When properly aligned, the guide member is fixed to the anterior side of the proximal tibia with pins. The tibia is then resected with an oscillating saw inserted through slots in the guide member.

Rohr, U.S. Pat. No. 4,566,448, discloses a ligament tensor device having a first member to engage the tibia and a second member to engage the intercondylar notch of a femur and a means for moving the second means with respect to the first means for applying a selected tension to the ligaments of the joint. Additionally, the invention includes cutting guide slots for guiding the cutting of the femoral condyles.

Keller, U.S. Pat. No. 4,586,496, discloses a surgical chisel having a flexurally rigid chisel shank and a thin, elongated chisel blade fixed at its front end. A chisel guide is provided having slides for displaceably guiding the blade and shank in a longitudinal direction.

Kenna, U.S. Pat. Nos. 4,653,488 and 4,787,383, disclose a tibial cutting jig for cutting a tibia after the femur has been resected. The tibia is aligned off of the resected femur through longitudinal traction and manipulation to bring the ankle under the femur to produce a tibial angle of 2.5 degrees resulting in an overall valgus alignment. The alignment is verified by sight. The knee joint is then immobilized, the transverse tibial cutting jig is pinned to the tibia, the knee is moved to flexion, and the tibia is cut by resting the saw blade on the top surface of the cutting jig.

Russell, et al., U.S. Pat. No. 4,722,330, discloses a distal femoral surface guide for mounting on an intramedullary alignment guide for use in shaping the distal femoral surface. A conventional shaping means such as an oscillating saw or hand saw is introduced into slots in the surface guide to resect the femur. The device also includes stabilizing members that extend along the sides of the femur to stabilize the device.

Fargie, et al., U.S. Pat. No. 4,736,737 discloses a tibial cutting jig having a base that interconnects with an intramedullary alignment rod installed along the axis of the tibia. The base includes outriggers carrying measurement keys for spacing the base a preselected distance above the tibia. A saw guide having slots is attached to the base and is positioned to allow for the cutting of the tibia, by means of an oscillating saw, at a selected position.

Zarnowski et al., U.S. Pat. No. 4,892,093, discloses a cutting guide for a saw blade for resecting a femur. The device is attached to a femur after the distal end has been removed and a transverse surface has been established. The cutting guide includes a base member having a planar base surface. A pair of laterally spaced-apart locating and securing posts are integral with the base member and project in a direction normal to the base surface to interconnect with the femur. Guide members in the form of cylindrical bars are positioned within side members attached to the base. A saw blade may be inserted between the guide surfaces to properly position the blade to cut the femur.

Vandewalls, U.S. Pat. No. 4,896,633, discloses a drill for drilling a hole into a femur. The device includes a positioning mechanism to firmly engage the outer peripheral surface of the femoral head and the femoral neck. This immobilizes the drill bushing relative to the femur and orients the axis of the drill with the central axis of the femur.

Whiteside, et al., U.S. Pat. No. 5,002,545, discloses a shaping device for shaping the tibial plateau comprising an alignment rod located anterior to the anterior cruciate ligament and along the anterior cortex of the intramedullary canal of the tibia. The shaping guide is interconnected with the rod and is adjustable with respect to the rod to control the amount of resection of the tibial plateau by raising or lowering the cutting guide surfaces. The device includes a pin which is inserted into a hole on the alignment guide for setting rotation alignment by aligning the pin with the intercondylar notch of the femur.

Schmidt, U.S. Pat. No. 5,049,149, discloses a sawing gauge system for intertrochantery accommodation osteotomies for removing a wedge-shaped section of bone with a predetermined wedge-angle so that an optimal pre-stress load F can act.

Lackey, U.S. Pat. No. 5,053,037, discloses a femoral drill guide with interchangeable femoral collets, a femoral reamer and a femoral anterior/posterior cutting block with an adoptable anterior femoral ledge. A plurality of diagonal slots are provided for making diagonal cuts in the distal end of the femur.

Ferrante et al. U.S. Pat. No. 5,098,436, discloses a modular guide for shaping a femur comprising a first bracket defining a generally U-shaped structure having an internal surface adapted to be seated on the distal aspect of a resected femur bone and an elongated central opening appointed to expose a selected area of the resected femur, including a curved track for guiding a first shaping tool along a predetermined path for controlled shaping of a curved patellar groove and a portion of the selected area exposed through the opening. A second bracket defines a linear slotted bore extending generally parallel to the long axis of the femur for guiding a second shaping tool to form a relatively deep recess accommodating an intercondylar-stabilizing housing of a knee implant.

Brown, U.S. Pat. No. 5,234,432, discloses a method of cutting the proximal end of a femur prior to cementing in a prothesis for reconstructive hip surgery.

Poggie, et al., U.S. Pat. No. 5,250,050 discloses an apparatus for use in preparing the bone surfaces for a total knee prothesis, comprising cutting guides, templates, alignment guides, a distractor and clamping instruments. The instrument for alignment of the cutting surface for resecting the tibia includes an ankle clamp, an adjustable alignment rod, and a cutting platform. After the cutting platform is properly aligned on the tibia, it is pinned thereto and the tibia may be resected using an oscillating saw. Also disclosed is a patella resection guide comprising a scissor-type clamp having distal gripping arms, each of which define a cutting surface, and gripping teeth.

Caspari, et al., U.S. Pat. Nos. 5,263,498, 5,228,459, and 5,304,181 disclose a method and apparatus for orthoscopically preparing bone surfaces for a knee replacement. A tibial jig is attached to the tibia at just above the ankle at a lower end and to just below the tibial tubercle at an upper end. One portal is formed in the knee for insertion of an orthoscope for viewing the knee, and another portal is formed for introducing resecting instruments. A cutting platform is aligned and secured in position and a cutting module is attached. Initially, a plunge cut across the tibial eminence is produced. This procedure is repeated until the surface of the tibial plateau is covered with trails having ridges therebetween. Thereafter, the device is passed back and forth over the tibial plateau to remove the ridges.

Morgan, U.S. Pat. No. 5,269,786, discloses a PCL oriented placement tibial guide method for guiding the tibial tunnel placement both inside and outside the knee in endoscopic ACL reconstruction.

Mikhail, U.S. Pat. No. 5,284,842, discloses a universal patellar clamp having an articular surface clamping member with a central aperture defining a centerline axis. An anterior clamping member is positioned along the centerline axis and is movable with respect to the articular clamping member to effect clamping of the patella for accepting a reamer for reaming a cavity in the patella of sufficient size to receive a patellar implant.

Johnson et al., U.S. Pat. No. 5,306,276, discloses a tibial resector guide including a tibial alignment jig having an ankle adjustment mechanism, a telescoping rod and a tibial resector guide which includes a head having a slot for receiving a bone saw. The head includes angled side walls along the slot which permit the guide to have a narrow anterior aperture, yet allow the saw blade to completely pass through the tibia.

Peterson, U.S. Pat. No. 5,342,368, discloses an intramedullary tibial resector guide which is affixed to the tibia by means of an intramedullary rod. An elongated bar extends from the intramedullary rod and carries a sleeve that supports a saw guide having a slot for receiving an oscillating saw.

Whitlock, et al., U.S. Pat. No. 5,147,365, discloses a patella osteotomy guide comprising a plier-like appliance with curved jaws for grasping a patella. A row of teeth face inwardly from the jaws and a rotating calibrated stylus measures the position of the patella with respect to an integral saw capture slot in each of the jaws. The jaws are curved with concave inner sides generally corresponding to the shape of a patella. With the guide attached to a patella, a sagittal saw can be passed through the saw capture slots to cut away a portion of the patella.

Additionally, Whiteside, U.S. Pat. No. 4,474,177 describes instruments for creating the distal femoral surfaces where a guide is used to index a flat surface used to guide the distal femoral resection. Kaufman, et al. U.S. Pat. No. 4,721,104 describes a method of preparing the intracondylar area of the distal femur. Jellicoe, U.S. Pat. No. 5,047,032 utilizes a side cutting drill to form the distal femoral surface.

None of these previous efforts, however, disclose all of the benefits and advantages of the present invention, nor do these previous patents teach or suggest all the elements of the present invention.

OBJECTS AND SUMMARY OF THE INVENTION

It is a primary object of the present invention to provide a method and apparatus for removing material from bones.

It is another object of the present invention to provide a method and apparatus for properly resecting bone.

It is also an object of this invention to provide a method and apparatus for properly orienting a resection of a bone.

It is a further object of the present invention to provide a method and apparatus to properly orient the resection apparatus with respect to a bone.

It is an additional object of the present invention to provide a method and apparatus for properly locating a bone resection.

It is a further object of the present invention to provide a method and apparatus to properly locate the resection apparatus with respect to a bone.

It is even another object of the resection apparatus of the present invention to provide a guide device and method of use thereof for establishing the location and orientation of the resection apparatus with respect to a bone.

It is an additional object of the present invention to provide a method and apparatus for making a curvilinear bone resection.

It is still a further object of the resection apparatus of the present invention to lessen the chances of fatty embolisms.

It is even further object of this invention to provide a method and apparatus capable of forming or re-forming some or all of the surfaces or resected surfaces of a bone.

It is another object of the present invention to provide a method and apparatus which is simple in design and precise and accurate in operation.

It is also an intention of the present invention to provide a method and apparatus for determining the location of the long axis of a bone while lessening the chances of fatty embolism.

It is also an object of the present invention to provide a method and apparatus to physically remove material from a bone in a pattern.

It is an additional object of the present invention to provide a method and apparatus to physically remove material from a bone in a pattern dictated by a pattern device and/or the geometry of a cutting device.

It is even another object of the resection apparatus of the present invention to provide a cylindrical or semi-cylindrical cutting device and method of use thereof for removing material from a bone.

It is also an object of the present invention to provide a method and apparatus for easily and accurately resecting a bone.

It is also an object of the present invention to provide a method and apparatus for resecting a bone which minimizes the manual skill necessary to complete the procedure.

It is even another object of the present invention to provide a method and apparatus for resecting a bone which is easy to use.

It is still yet another object of the present invention to provide a method and apparatus for resecting a bone which minimizes the amount of bone removed.

It is a further object of the present invention to provide a method and apparatus for resecting a bone which allows one to visually inspect the location of the cut or cuts prior to making the cut or cuts.

It is yet a further object of the present invention to provide a method and apparatus for resecting a bone which physically removes material from the bone along a surface dictated by a guide device.

It is still a further object of the present invention to provide a method and apparatus for resecting a bone which employs a milling bit or form cutter for removing material from the bone.

It is even another object of the present invention to provide a method and apparatus for removing material from a bone such that both the cutting path and cutting profile are predominantly curvilinear.

These objects and others are met by the method and apparatus for bony material removal of the present invention.

Many of the specific applications of the method and apparatus of the present invention described herein apply to Total Knee Replacement, a surgical procedure wherein planar surfaces and/or curvilinear surfaces must be created in or on bone to allow for proper attachment or implantation of prosthetic devices. However, it should be noted that it is within the scope of the present invention to apply the methods and apparatus herein described to the removal of any kind of material from bones in any other application where it is necessary, desirable or useful to remove material from bones.

The apparatus of the present invention comprises a number of components including a positioning apparatus, a pattern apparatus and a cutting apparatus.

The pattern apparatus is oriented and located by the use of the positioning apparatus which references the geometry of a bone to be resected and/or other anatomic landmarks. When used to resect a distal femur, the positioning apparatus also references the long axis of the femur. Once the positioning apparatus has been properly located, aligned, and initially fixed in place, the pattern apparatus may be attached thereto, and then adjusted according to the preferences of the surgeon utilizing the apparatus, and then the pattern apparatus can be rigidly fixed to a bone to be resected. This ensures the pattern apparatus is properly located and oriented prior to the use of the cutting apparatus to remove material from the bone.

More specifically, when the method and apparatus of the present invention are used in connection with resecting a distal femur, the positioning apparatus is located and aligned utilizing the intramedullary canal of the femur, (thereby approximating the long axis of the femur), the distal surfaces of the femoral condyles, the anterior surface of the distal femur, and the posterior surfaces of the femoral condyles which are referenced to indicate the appropriate location and orientation of the pattern apparatus. Fixation means may be used to fix the positioning apparatus, as well as the pattern apparatus to the distal femur. Means may be present in the positioning apparatus and/or pattern device for allowing the following additional adjustments in the location and orientation of the pattern device:

1. internal and external rotational adjustment;
2. varus and valgus angular adjustment;

3. anterior and posterior location adjustments;

4. proximal and distal location adjustment; and 5. flexion and extension angular adjustment.

Cannulated screws, fixation nails or other fixation means may then be used to firmly fix the pattern apparatus to the distal femur. The positioning apparatus may then be disconnected from the pattern apparatus and removed from the distal femur. Thus, the location and orientation of the pattern apparatus is established.

The pattern device possesses slot-like features, or a cutting path, having geometry that matches or relates to the desired geometry of the cut. When used in connection with resecting a knee, the cutting path resembles the interior profile of the distal femoral prosthesis. The cutting path, guides the cutting apparatus to precisely and accurately remove material from the distal femur. Thus the distal femur is thereby properly prepared to accept a properly aligned and located distal prosthesis.

In preparing a patella, the pattern device may be an integral part of the positioning apparatus which is oriented and located by referencing the geometry of the patella itself as well as the structures of the patellofemoral mechanism to determine the location and orientation of a predominantly planar resection. The cutting device may then be employed to perform the resection of the patella by traversing the path dictated by the pattern device, thus dictating the final location and orientation of the patella prosthesis.

The basic apparatus and method of the present invention is disclosed in the copending patent applications set forth in the Related Applications section of the present application, and the entire disclosures of these related applications are expressly incorporated herein by reference.

BRIEF DESCRIPTION OF THE DRAWINGS

Other important objects and features of the invention will be apparent from the following Detailed Description of the Invention taken in connection with the accompanying drawings in which:

FIG. 9 is an exploded perspective view of the protractor rod guide assembly portion of the positioning apparatus shown in FIG. 6.

FIG. 22 is a side plan view of another embodiment of the pattern apparatus and positioning apparatus of the present invention for resecting a patella.

FIG. 23 is a top plan view of the patella resection apparatus shown in FIG. 22.

FIG. 24 is a front plan view of the patella resection apparatus shown in FIG. 22.

DETAILED DESCRIPTION OF THE INVENTION

As shown generally in FIGS. 1–5, the pattern apparatus of the present invention, generally indicated at 30, comprises pattern plates, generally indicated at 32, and cross bar apparatus, generally indicated at 40.

Pattern Plates

Pattern plates 32 include fixation apertures 34 extending therethrough for accepting fixation means, as will hereinafter be described, for affixing the pattern plates 32 to a bone. The pattern plates 32 further include a cutting path 36 for dictating the path along which a bone is to be cut. As shown in FIGS. 1–5, which are directed to an embodiment of the present invention for resecting a distal femur, the cutting path 36 in the pattern plates 32 matches the profile of a femoral component of a knee prosthesis for resecting the femur to accept the femoral component of the prosthesis. Importantly, as will hereinafter be described, the cutting path 36 could be identical in size and shape to an interior bearing surface of a femoral component of the knee prosthesis, or could vary in size and shape in accordance with alternative methods and apparatus used to perform the resection. For example, the cutting path could be larger than the desired resection, but a larger cutting tool could be used to arrive at a resection of the desired the desired size.

Figure 3:
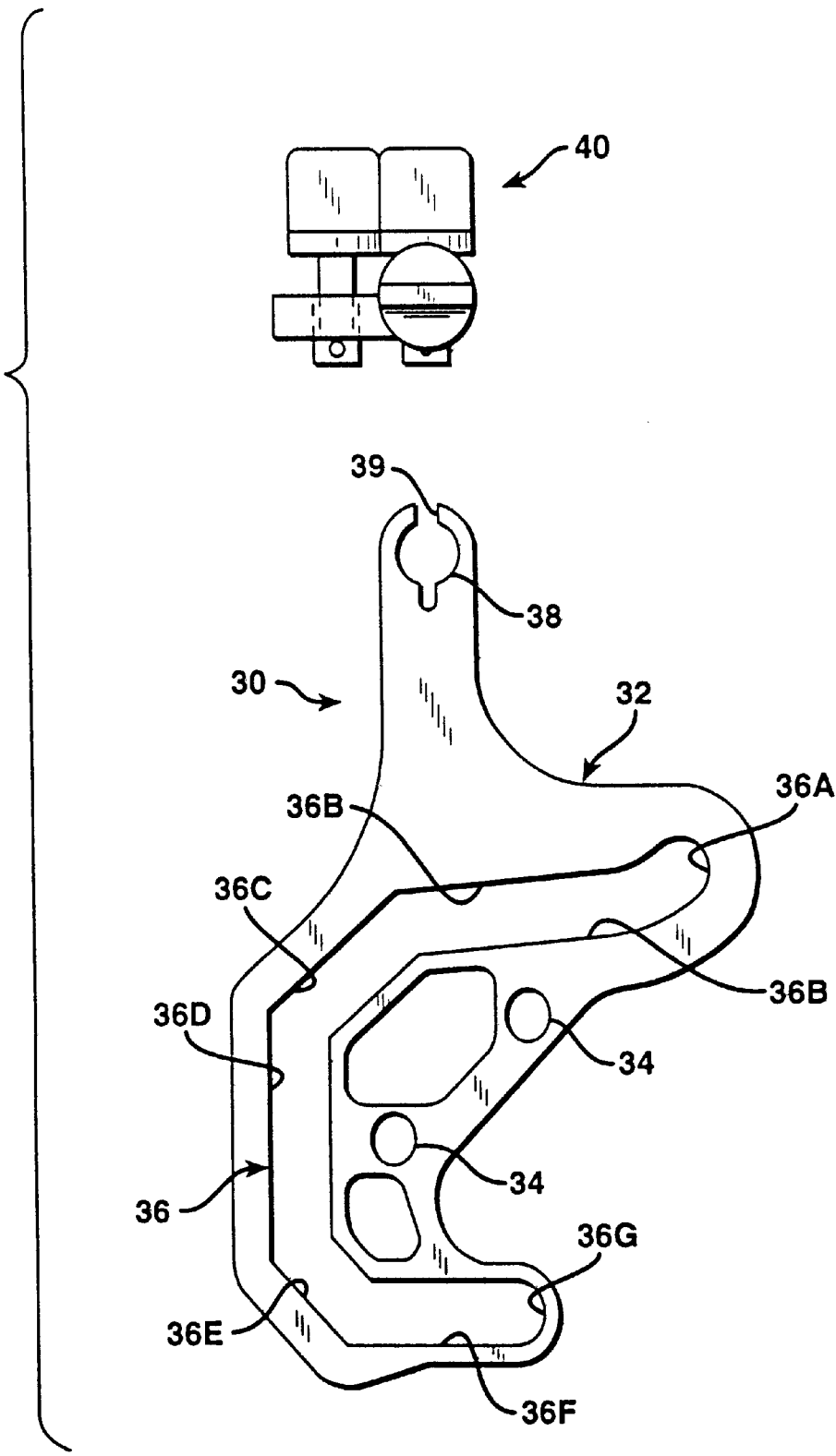
FIG. 3 is a partially exploded side plan view of the positioning apparatus shown in FIG. 1.
Figure 4:
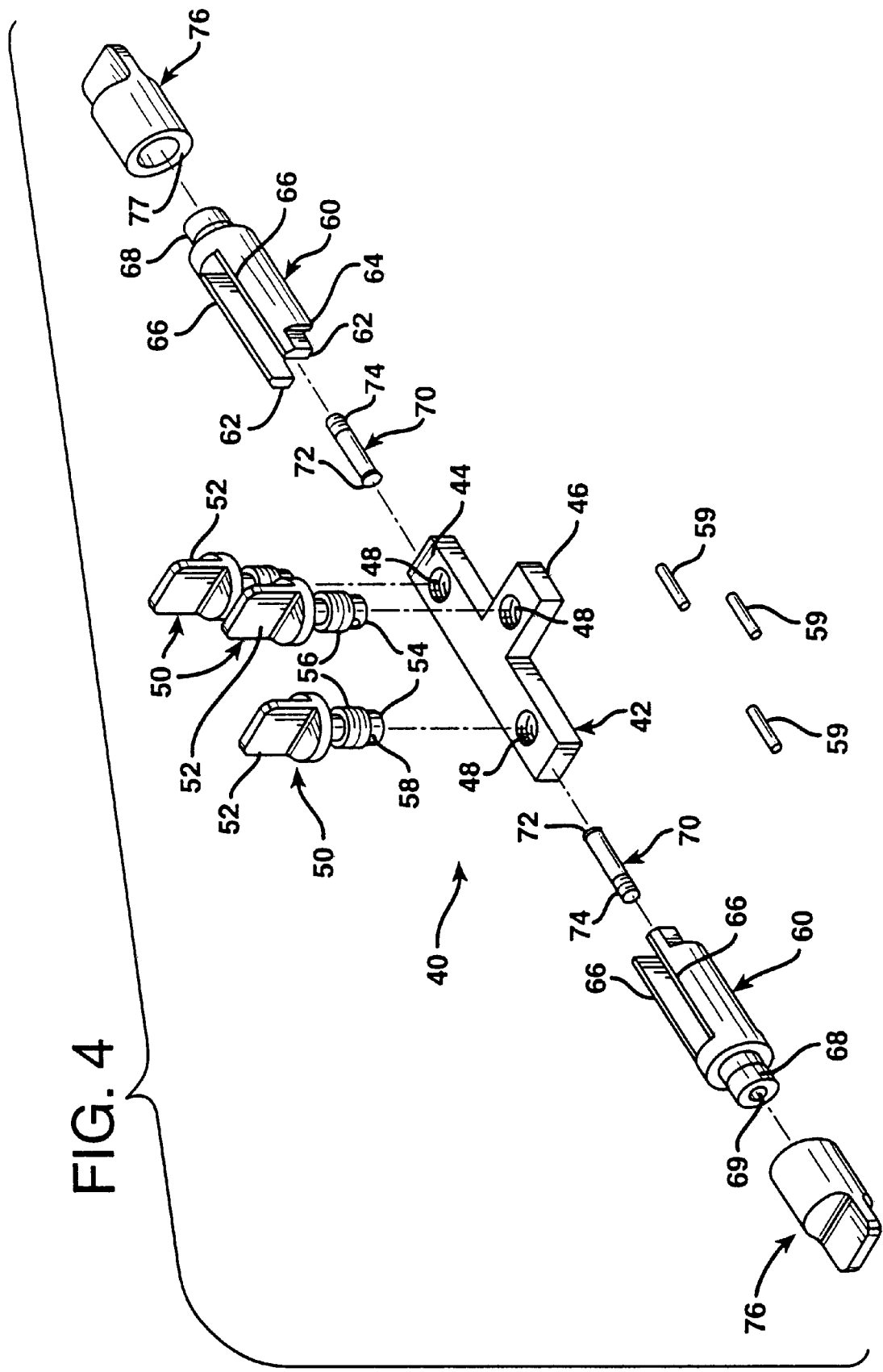
FIG. 4 is an exploded perspective view of the cross bar of the pattern apparatus shown in FIG. 1.
Figure 5:
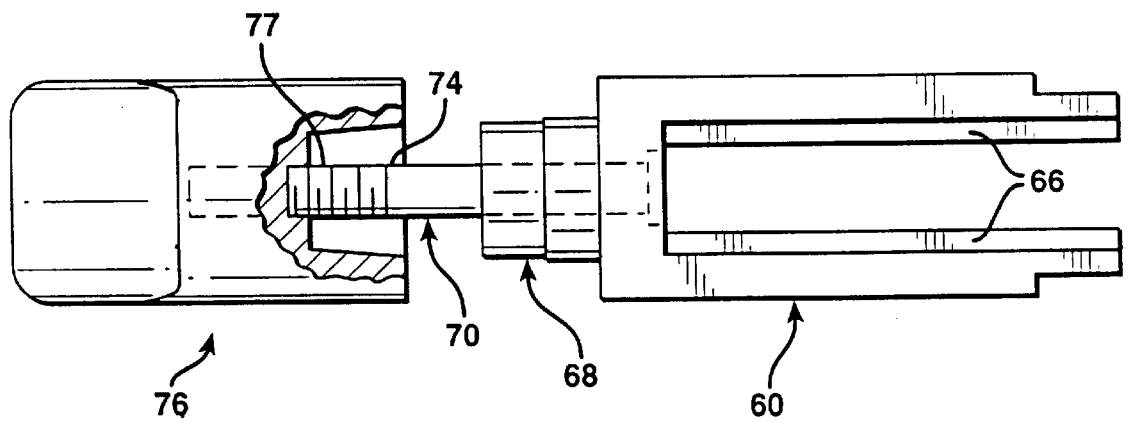
FIG. 5 is a partially cut away side plan view of the pattern plate/cross bar attachment linkage for interconnecting the pattern plate to the cross bar as shown in FIG. 1.
Figure 6:
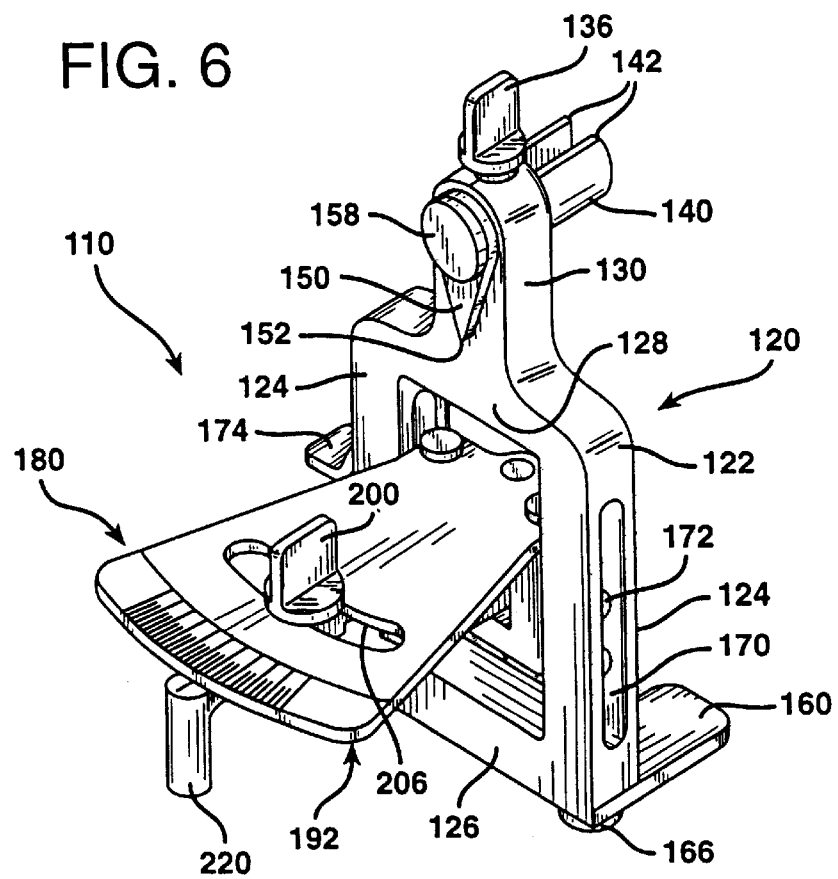
FIG. 6 is a perspective view of the positioning apparatus of the present invention.
Figure 7:
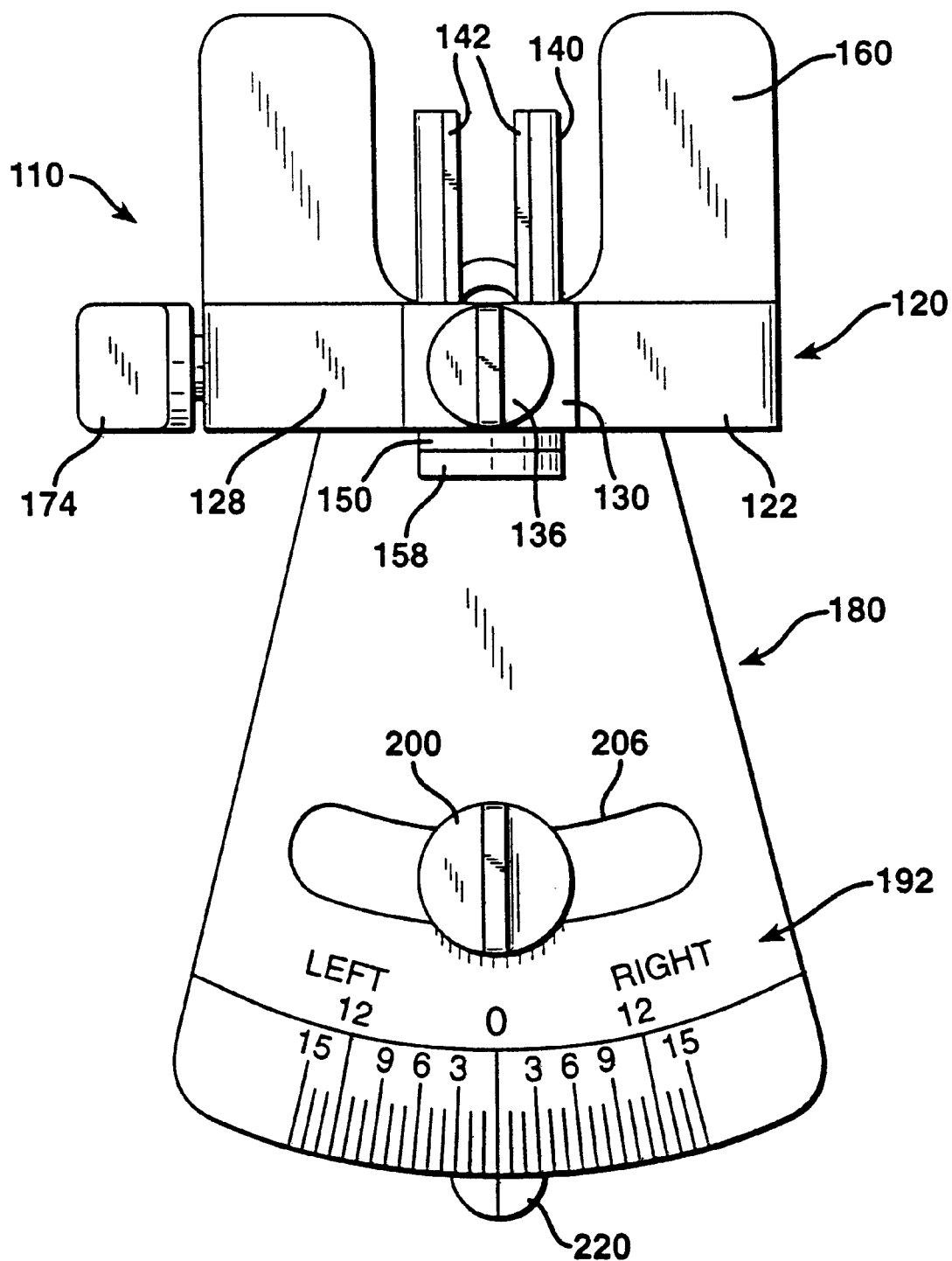
FIG. 7 is a top plan view of the positioning apparatus shown in FIG. 6.
Figure 8:
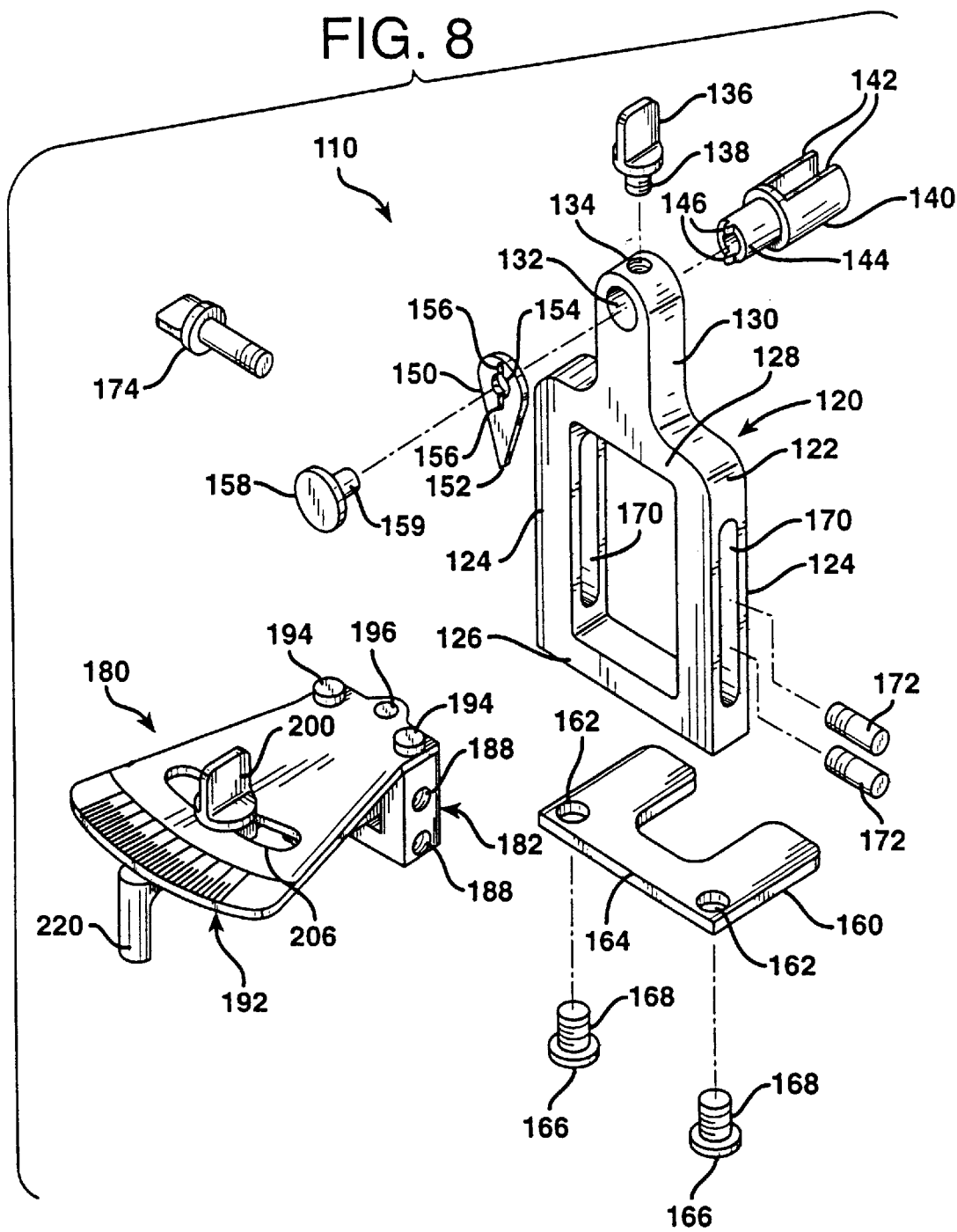
FIG. 8 is an exploded perspective view of the positioning apparatus shown in FIG. 6.
Figure 10A:
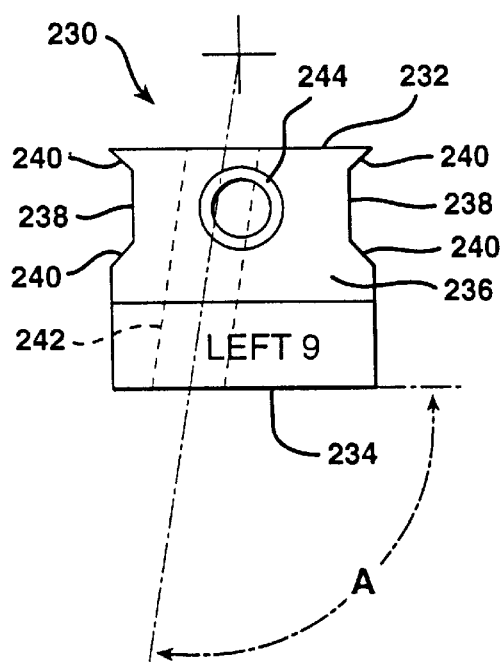
FIGS. 10A–10D are plain views of another embodiment of a rod guide assembly for use with the positioning apparatus shown in FIG. 6.
Figure 10B:
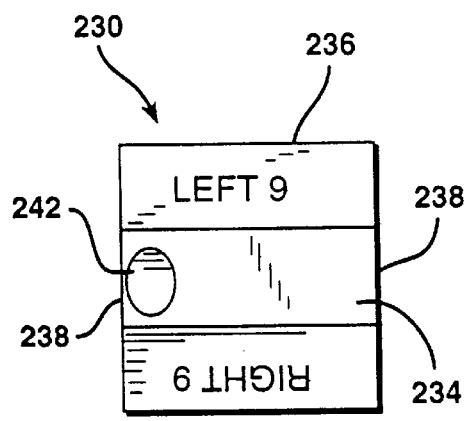
Figure 10C:
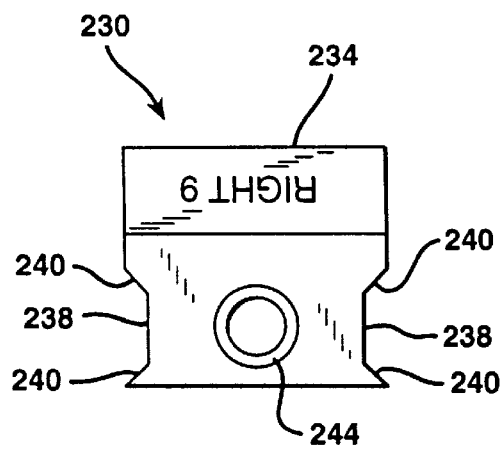
Figure 10D:
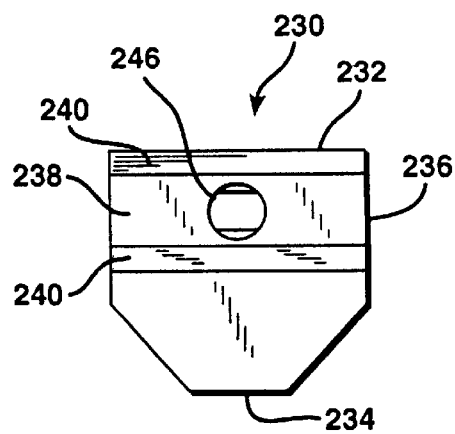

In the embodiment of the present invention shown in FIG. 3, the cutting path 36 includes an anterior end 36A, an anterior cut portion 36B, an anterior chamfer portion 36C, a distal cut portion 36D, a posterior chamfer portion 36E, a posterior cut portion 36F, and a posterior end 36G. Alternatively, the cutting path 36 could of any desired shape in accordance with the prosthesis systems of the various manufacturers of such prosthesis, the desires of the surgeon utilizing the apparatus and/or the application for which a bone is to be cut.

Figure 1:
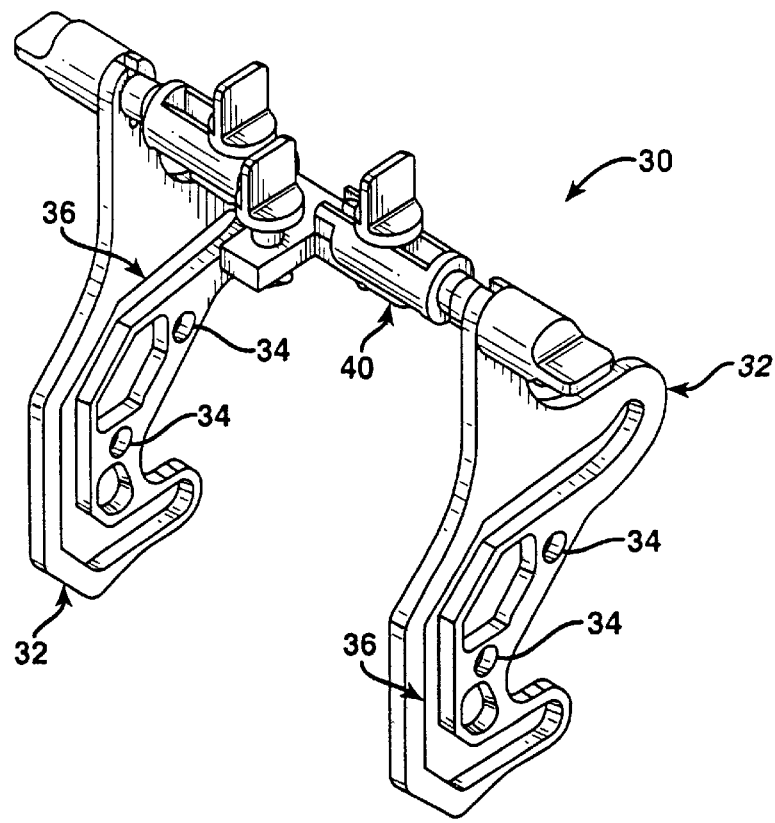
FIG. 1. is a rear perspective view of an embodiment of the pattern apparatus of the present invention.
Figure 2:
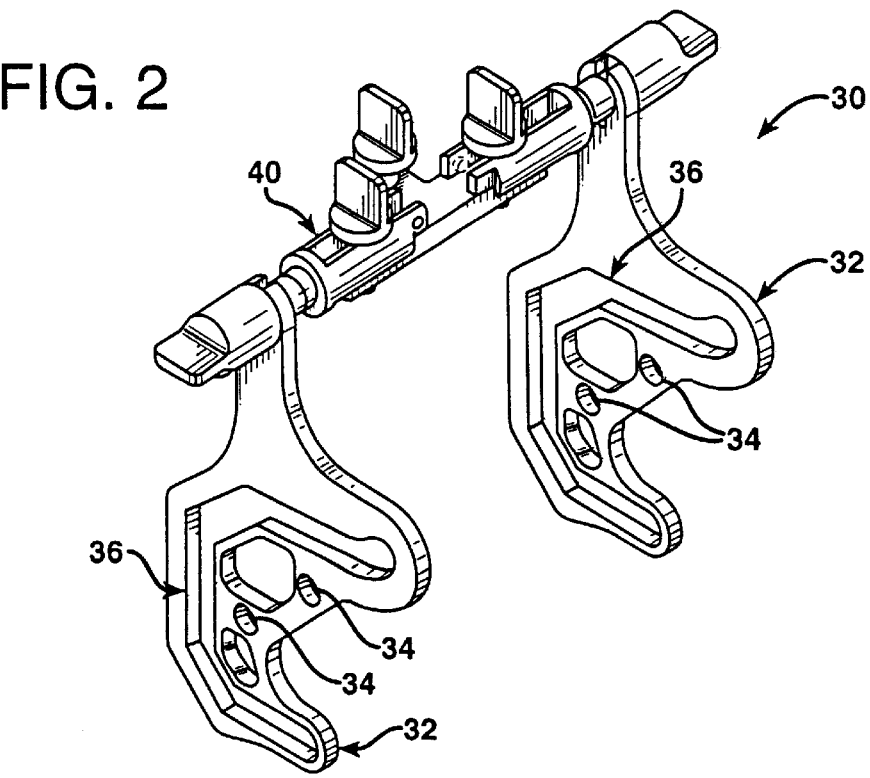
FIG. 2 is a front perspective view of the pattern apparatus shown in FIG. 1.

Although a single pattern plate 32 may be employed in resecting a femur or other bone (and in some cases, i.e. a partial femur resection, it may be preferable to employ a single pattern plate 32), two pattern plates 32 are generally employed to coact with each other to support a cutting means on two sides of a bone to be cut. In the case of resecting a femur, a preferred embodiment of the present invention, as shown in FIGS. 1–3, comprises two pattern plates 32 positioned on opposing sides of a femur. The pattern plates 32 are interconnected with each other, and maintained in proper alignment with respect to each other by a cross bar apparatus generally indicated at 40, to straddle a bone. The pattern plates 32 include cross bar apertures 38 for interconnecting with the cross bar apparatus 40. The pattern plates may also include cross bar slots 39 for permitting quick connect/disconnect between the pattern plates 32 and the cross bar apparatus 40. Of course, it should be noted that the pattern plates 32 could interconnect with the cross bar in any other manner known in the art, or especially with bone cutting applications other than resecting the femur, the pattern plates 32 could be used without a cross bar.

Cross Bar Apparatus

The cross bar apparatus 40 includes a number of component parts, namely, T-bar 42 having a top 44 and a stem 46 interconnected with and extending from the top 44 in the same plane. The T-bar 42 shown in the Figures comprises a flat metal member having a uniform rectangular cross-section through both the top 44 and the stem 46. Three threaded lock apertures 48 are formed through the T-bar 42, one at each end of the top 44 and at the far end of the stem 46. Lock screws 50, having gripable heads 52 and shafts 54 with threaded waists 56, threadably engage the threaded lock apertures 48 in the T-bar 42. The lock screws 50 further include pin holes 58 extending radially through the shafts 54 at the terminal ends thereof for receiving pins 59 for capturing the lock screws 50 on the T-bar 42.

The cross bar apparatus 40 further includes linkages 60 having a first end for interconnection with the T-bar 42 and a second end for supporting and engaging pattern plates 32. The first ends of the linkage 60 include a lower flat surface 62 for contacting the T-bar 42, overhanging shoulders 64 for contacting the sides of the T-bar 42, and an upper flat surface 66 for contact with the lock screws 50 for locking the linkages 60 onto the T-bar 42. As shown in detail in FIG. 5, the second ends of the linkage 60 include cylindrical supports 68 for supporting the pattern plates 32 thereon. The cylindrical supports 68 include axial extending apertures 69 for receiving capture pins 70 therethrough, the capture pins 70 including flanged ends 72 and threaded ends 74. The capture pins 70 serve to capture pattern lock nuts 76 on the linkages 60, the capture pins 70 extending through the axial apertures 69, the flanged ends 72 retaining the capture pins 70 therein, the threaded ends 74 extending out of the cylindrical supports 69 and into the threaded interior 77 of the pattern lock nuts 76. The cylindrical supports 68 receive the cross bar apertures 38 of the pattern plates 32 and the pattern lock nuts 76 are threaded down onto the capture pins 70 to secure the pattern plates 32 to the cross bar apparatus 40. Of course, other embodiments of the cross bar apparatus sufficient for supporting the pattern plates of the present invention are considered within the scope of the present invention.

Positioning Apparatus

As shown in FIGS. 6–10, the positioning apparatus of the present invention is generally indicated at 110. The positioning apparatus generally comprises positioning body 120 and alignment apparatus 180. The positioning body 120 comprises a frame 122 having sides 124, bottom 126 and top 128 arranged to form a frame having a rectangular aperture defined therewithin. The top 128 further includes a head 130 formed thereon having a linkage aperture 132 extending therethrough at an upper end thereof, and having a lock aperture 134 extending from the upper edge of the head to the linkage aperture 132. A lock screw 136 having a threaded shaft 138 extends into and is threadably engaged with the lock aperture 134 for locking the head 130 to a linkage, namely cross bar linkage 140. Cross bar linkage 140 includes a first end having an upper flat surface 142 for interconnecting with the cross bar in a manner similar to the pattern plate linkages for attaching the pattern plates to the cross bar as hereinbefore described. The cross bar linkage 140 further includes a shaft 144 which is received by the linkage aperture 132 in the head 130 to interconnect the positioning body 120 with the cross bar linkage 140 and hence with the cross bar apparatus 40 and the pattern apparatus 30. The positioning body can then be locked onto the cross bar linkage 140 by means of lock screw 136.

The end of shaft 144 of the cross bar linkage 140 includes projections 146 extending axially from the shaft 144. When the shaft 144 is positioned in the linkage aperture 132, the projections 146 extend beyond the frame 122 and are received in slots 156 in alignment indicator 150 for keying the orientation of the alignment indicator 150 with the alignment of the cross bar linkage 140, and hence with the alignment of the cross bar apparatus 40 and the pattern apparatus 30. The alignment indicator 150 includes an alignment arrow 152 for indicating alignment on a scale that may be set forth on the positioning body 120. An indicator pin 158 having a shaft 159 may be employed to pin the alignment indicator 150 to the cross bar linkage 140.

Attachable to the bottom 126 of the positioning body 120 is skid 160. The skid 160 includes skid apertures 162, one of which may include an aperture flat 164 for insuring proper alignment and positioning of the skid 160 with respect to the positioning body 120. The skid 160 is attached to the bottom 126 of the positioning body 120 by means of skid bolts 166 having threaded shafts 168 which coact with threaded apertures in the bottom 126 of the positioning body 120. Of course, the skids could be formed integrally as part of the positioning body.

The sides 124 of the positioning body 120 include slots 170 extending in a facing relationship along the sides 124. The slots extend from exterior surfaces of the sides to interior surfaces thereof, i.e. to the interior rectangular aperture formed within the positioning body 120.

Alignment Apparatus

The alignment apparatus 180 interconnects with the positioning body 120 by means of alignment guide body 182 which is a U-shaped member having sides 184 and a bottom 186. The alignment guide body 182 is sized to fit within the rectangular aperture formed within the positioning body 120. The alignment guide body 182 is retained within the positioning body by means of guide studs 172 that extend through the sides 124 of the positioning body 120 within the slots 170 and into guide apertures 188 at one side of the alignment guide body 182. At the other side of the alignment guide body 182 a lock stud 184 extends through the slot 170 in the side 124 of the positioning body 120 and into a threaded lock aperture 189 in the alignment guide body 182. The guide studs 172 and the lock stud 174 coact to maintain the alignment guide body 182 within the positioning body 120, and the lock stud 174 can be threaded down to lock the vertical position of the alignment guide body 182 with respect to the positioning body 120.

At upper ends 190 of the sides 184 of the alignment guide body 182 are plate apertures 191. The alignment plate 192 includes bolt apertures 195 aligned with the plate apertures 191 of the alignment guide body 182, and plate bolts 194 extend through the bolt apertures 195 in the alignment plate 192 and into the plate apertures 191 to secure the alignment plate 192 to the alignment guide body 182. The alignment plate 192 further includes rod guide aperture 197 which receives rod guide bolt 196 therethrough to interconnect the alignment plate 192 with the IM rod guide 210 as will hereinafter be described. Additionally, the alignment plate 192 includes lock slot 206 extending through the alignment plate 192 along an arc for purposes hereinafter described.

The IM rod guide 210 includes IM rod aperture 212 for receiving an IM rod therethrough. The IM rod guide 210 is interconnected at a forward end with the alignment plate 192 by means of plate attachment aperture 214 on the rod guide 210 which receives rod guide bolt 196 therein after such bolt 196 passes through the alignment plate 192 to secure the rod guide 210 in a pivoting relationship with respect to the alignment plate 192 at forward ends of the rod guide 210 and the alignment plate 192. The IM rod guide 210 is additionally interconnected with the alignment plate 192 by rod guide lock bolt 200 which includes a threaded shaft 210 and pin aperture 202. The rod guide lock bolt 200 extends through the slot 206 in the alignment plate 192 and through threaded lock bolt aperture 216 in the rod guide 210 where it is captured by means of capture pin 218 extending through the pin aperture 202. The IM rod guide further includes rod guide handle 220 which is configured to be easily manipulated.

The alignment plate 192 further includes a printed angular rotation scale which indicates the degree of angular rotation between the rod guide 220 and the alignment apparatus, and hence the angular rotation between the IM rod and the positioning body 120. After such alignment is determined, it can be locked into place by tightening down rod guide lock bolt 200. Thereafter, with such angular rotation fixed, the pattern apparatus 30 can be positioned with respect to the bone to cut, and the positioning apparatus 110 can be removed from interconnection with the IM rod and the pattern apparatus 30, the IM rod removed from the bone, and bone cutting can be initiated.

In another embodiment, as shown in FIGS. 10A, 10B, 10C and 10D, IM rod guide block 230 is used instead of the alignment plate 192 and the alignment guide body 182. The IM rod guide block 230 includes a rear surface 232, a front surface 234, a top surface 236 and sides 238. The sides 238 include retaining flanges 240 at the rear and front surfaces for retaining the IM rod guide block 230 within the rectangular aperture formed by the positioning body 120. The IM rod guide block 230 further includes IM rod aperture 242 extending through the block 230 from the rear surface 232 to the front surface 234 for accepting the IM rod therethrough. The rod aperture 242 extends through the guide block 230 at an angle A with respect to axis of the guide block for accommodating the varus/valgus orientation of the femur. The guide block 230 is part of set of blocks having rod apertures of various angles extending therethrough, i.e. 5, 7, 9, 11, 13 degrees, for use femurs having varying angles of orientation. The guide block 230 also includes lock aperture 246 for locking the proper vertical position of the guide block 230 with respect to the positioning body 220. The guide block 230 may additionally include two apertures 244 for accepting an anterior referencing arm for use in determining the anterior/posterior size of the femur. It should be noted that other alignment means for aligning the positioning apparatus with respect to a bone to be cut are considered within the scope of the present invention.

Fixation Means

Figure 11:
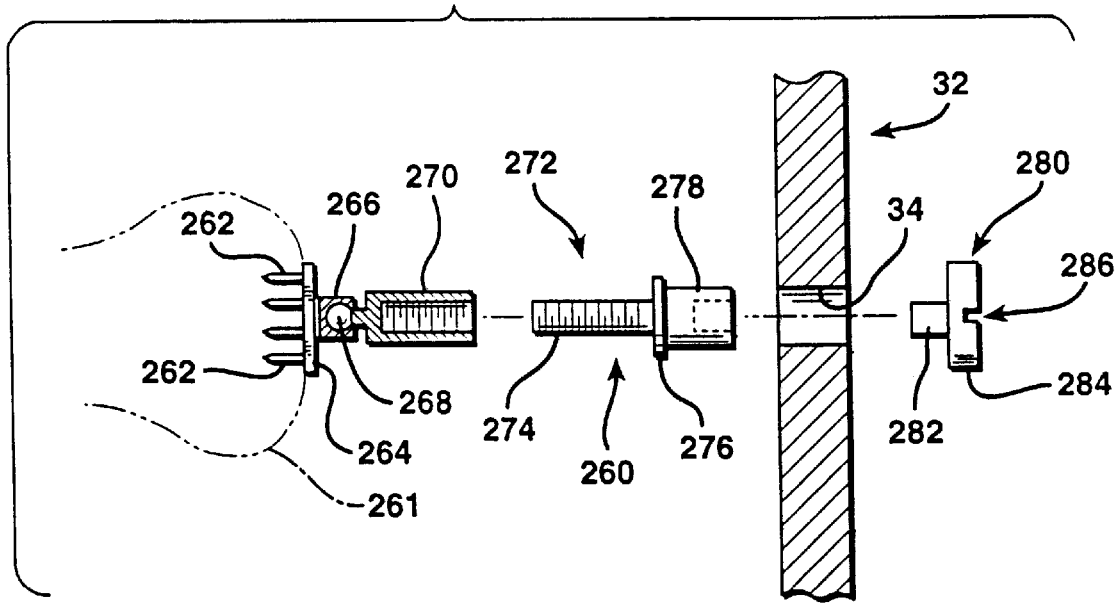
FIG. 11 is a side plan view of an embodiment of the fixation device for affixing the pattern apparatus shown in FIG. 1 to a bone.

Various fixation means, including those known in the art, can be used to fix the pattern plate or plates to the femur or other bone to be cut. FIG. 11 shows a preferred fixation means, generally indicated at 260. The fixation means 260 includes a spike plate 264 carrying on one side thereof a spike or spikes 262 for contacting, and even extending into, bone 261. At the other side of the spike plate 264 is spike plate socket 266 for receiving plate driving ball 268 in a keyed relationship therewith. The driving ball 268 is interconnected to an end of driving sleeve 270 and which has a threaded aperture extending therein from the opposite end thereof.

A driving screw 272 having a threaded shaft 274 coacts with the internally threaded driving sleeve 270 such that the rotation of the driving screw 272 either propels or retracts the driving sleeve 270, as well as the spike or spikes 262, with respect to the driving screw 272. The driving screw 272 further includes a captured head 278 and capture flange 276. The captured head 278 is received within a fixation aperture 34 in the pattern plate 32, the capture flange 276 preventing the captured head 278 from passing through the fixation aperture 34. A driving cap 280 is interconnected with the captured head 278 at the outside of the pattern plate 32. The driving cap 280 includes a shaft 282 received by the captured head 278, a flanged head 284 for contacting against the outside of the pattern plate 32, and a driver recess 286 of any desirable configuration for receiving driving means such as a flat, phillips or hex head driving means for driving the driving cap 280 to drive the driving screw 272 to move the spike or spikes 262 towards or away from a bone.

Importantly, this type of fixation means allows for fixation of the pattern plates 32 to even osteoporotic bones. Additionally, this fixation means is self adjusting to fit changing contours of bones. Further, because of its relatively low profile, this fixation means does not interfere with soft tissue about a bone to be cut. Other types of fixation means include cannulated screws, pins, spring loaded screws, capped screws, spiked screws and/or combinations thereof, all of which are considered within the scope of the present invention and could be used in connection with the present invention.

Anterior/Posterior Referencing

Figure 12:
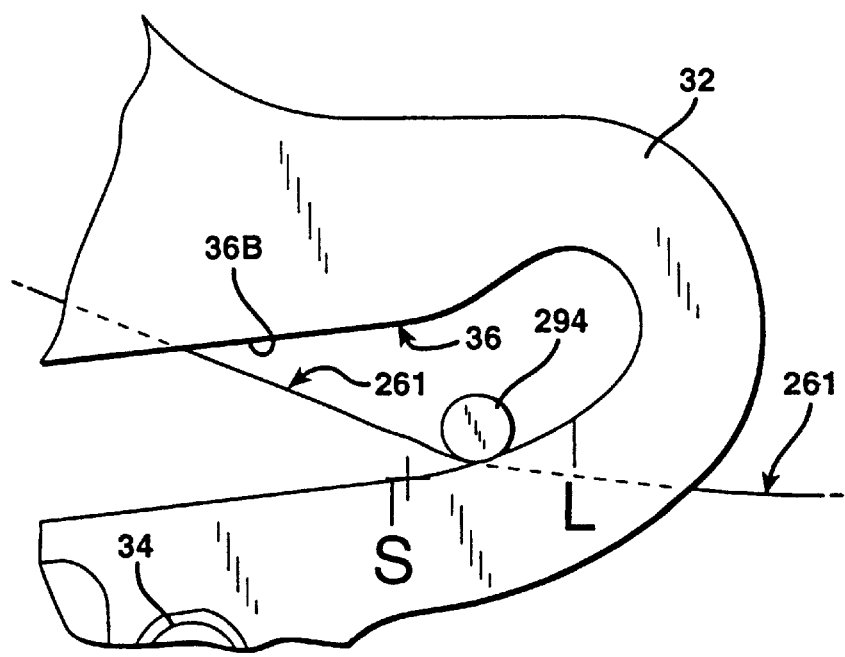
FIG. 12 is a partial side plan view of the pattern apparatus shown in FIG. 1, showing the posterior/anterior referencing guide.

The apparatus of the present invention further includes built-in anterior/posterior referencing means as shown in FIG. 12 for use in connection with preparation of the distal femur in Total Knee Replacement. As is known in the art, anterior/posterior referencing refers to proper positioning of the distal femur cuts with respect to the anterior and/or posterior sides of the femur or other bone to be cut.

The anterior/posterior difference between femoral implant sizes may vary by as much as 3 to 5 millimeters between sizes. Of course, many femurs are between sizes. Disregarding proper positioning of the cutting guide and the associated femur cuts could lead to flexion contracture (where the bone is slightly below size and the implant adds too much material to posterior side of femur which results in the inability to move the knee into flexion because the extra posterior material contacts the tibial implant components) and/or anterior notching of the femur (where the bone is slightly above size and the anterior runout point of the anterior cut is recessed in the anterior side of the bone in a sharp notch, thus seriously weakening the structural integrity of the distal femur, especially under cyclic fatigue or impact loading conditions).

Anterior referencing systems have a major advantage over posterior referencing systems in that they theoretically never notch the anterior cortex of the femur. The drawback of anterior referencing is that a slightly larger bone results in collateral ligament laxity in flexion and a slightly smaller bone will result in collateral ligament tightening in flexion (flexion contracture).

Posterior referencing systems have a major advantage over anterior referencing systems in that they theoretically never develop flexion contracture. The drawback is that a slightly large femur is prone to anterior notching, which can increase the likelihood of distal femoral fractures under either impact loading or cyclic fatigue loading.

Another approach to anterior/posterior referencing is a hybrid design that allows for both anterior and posterior referencing. The positioning apparatus 110 references the posterior femoral condyles (posterior referencing), while the pattern plates 32 allow for precise referencing of the anterior femoral cortex. The anterior referencing device can be as simple as that shown in FIG. 12 wherein a referencing pin 294 is placed through the anterior-most cutting paths 36 of the pattern plates 32 to contact the anterior femoral cortex 261. The pattern plates 32 include markings S (smaller size) and L (larger size). When the pin 294 falls between the S and L marks, the pattern plates 32 are the proper size and are properly positioned for that femur. If the pin 294 falls outside the range marked by S and L towards the S side, a smaller size pattern plate should be used, and conversely, if the pin 294 falls outside the range on the L side, a larger size pattern plate should be used. Alternatively, the pattern plate 32 could be adjusted vertically via means not shown to compensate for between size bones.

In another embodiment, the pattern plate could include a plunger assembly at the anterior end of the cutting path. The plunger could be movable vertically to contact the femur and indicate size of the femur with respect to the pattern plate in use. As such, the plunger could be incrementally marked from +4 to −4 millimeters with 0 being the proper size for the pattern plates in use. Again, the pattern plates could be sized up or down if the femur is off of the scale, or the pattern plates could be moved up or down to compensate for between size bones depending upon surgeon preference. If, for example, a bone registers a +2, anterior notching of the femur would occur. To avoid this, the pattern plates could be moved anteriorly 1 millimeter to +1. In this manner, anterior notching would be minimized and the posterior femoral condyles would only lack 1 millimeter of material, which should not be detrimental because some ligamentous laxity in flexion is acceptable because the collateral ligaments are normally slightly looser in flexion than they are in extension. It should be noted that the radii or curve in the anterior-most area of the cutting path will assure that anterior notching is easily avoidable.

Pattern Plate with Tracking Means

Figure 13:
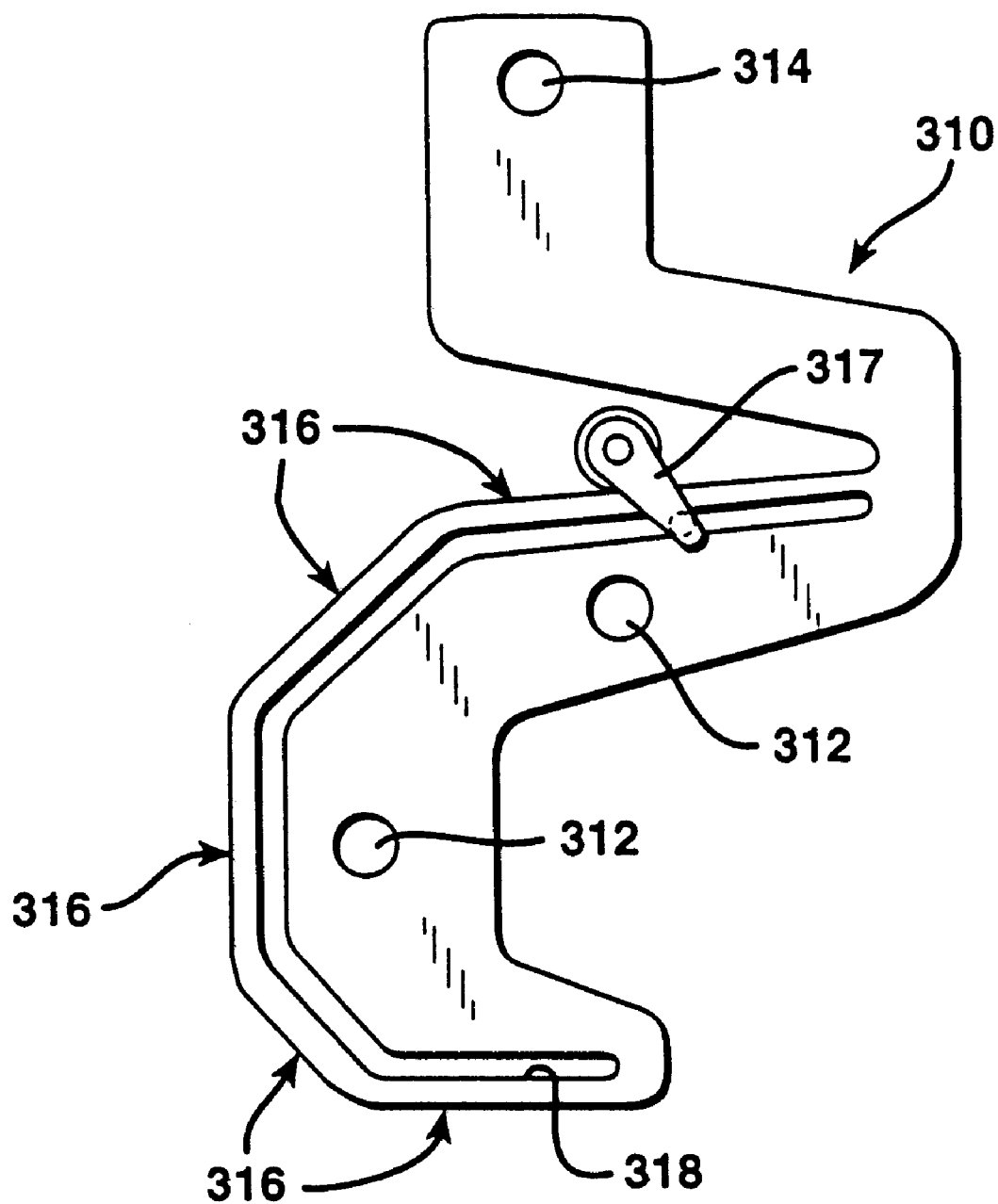
FIG. 13 is a side plan view of another embodiment of the pattern apparatus shown in FIG. 1.

Another embodiment of the pattern plates of the present invention is shown in FIG. 13. In this embodiment, the pattern plates, generally indicated at 310, basically comprise only the lower edge, or bearing surface 316 of the cutting path 36 of pattern plates 32 shown in FIGS. 1–3. Accordingly, the pattern plate 310 includes fixation apertures 312 and cross bar aperture 314. The milling apparatus bears against the bearing surface and follows the same therealong to resect the bone in accordance with the shape of the bearing surface 316. Of course, the bearing surface could be smaller or larger than the desired cut location depending on the size of the milling apparatus. The pattern plate 310 could further include a groove or guide means 318 extending in the pattern plate alongside the bearing surface and the milling apparatus could include an arm or other retaining linkage 317 extending from the handle or bushing of the milling apparatus and into the groove 318 for engagement with the groove 318 for guiding or retaining the milling apparatus along the bearing surface 316 of the pattern plate 310. Alternatively, it should be noted that the bearing surface could also comprise just the upper surface of the cutting path 36 of the pattern plates 32 shown in FIGS. 1–3.

Ligament Balancing

Figure 14:
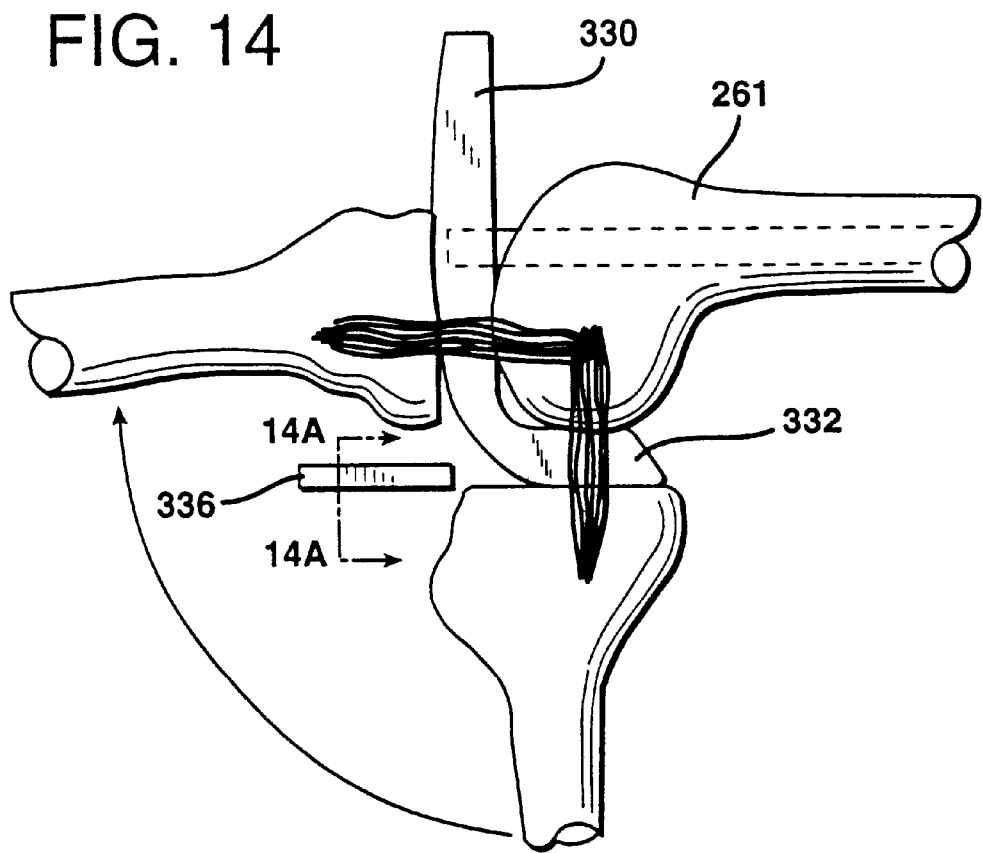
FIG. 14 is a side plan view of another embodiment of the positioning apparatus shown in Fig. 6 for use in performing ligament balancing.
Figure 14A:
FIGS. 14A and 14B are cross-sectional views along section A—A in FIG. 14.
Figure 14B:
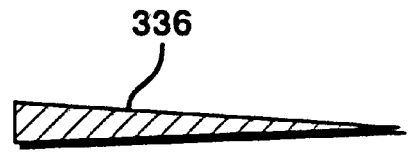

As shown in FIG. 14, an alternative embodiment of the alignment guide body 330 can be used for performing ligament balancing. The alignment guide body 330 of this embodiment can include a skid 332 formed as a part of the guide body 330, or attachable thereto. The skid 332 is of a relatively thick cross section, approaching or equal to the cross section of the guide body 330. The guide body 330 is attached to the femur 261 and the femur may be moved from extension to flexion and back, while the ligament tension of the collateral ligaments is reviewed. Ligamentous release can be performed to balance the ligaments. Further, shims 336, in either a rectangular cross section (FIG. 14A) or an angled cross section (FIG. 14B), can be used in connection with the alignment guide body 330 and skid 332. These shims could be positioned between the underside of the skid 332 and the resected tibia.

Milling Means

In a preferred embodiment of the invention, a cylindrical milling bit is used for following the cutting path described in the pattern plates for resecting a bone. Importantly, it is within the scope of the present invention to use a flat reciprocating bit, much like a hack saw, for following the cutting paths described in the pattern plates for resecting a bone.

Further, it may desirable to make all or some of the cuts using a cylindrical milling bit or a flat reciprocating bit having a smooth center section without cutting means. An advantage of a cutting tool without cutting means along a center portion thereof is the protection of posterior cruciate ligament during resection of the femur. Accordingly, one cutting tool could be used to make the anterior cut, the anterior chamfer, the distal cut and the posterior chamfer, while another cutting tool, with a smooth center portion, could be used to make the posterior cut to avoid any chance of jeopardizing the posterior cruciate ligament.

Additionally, the milling bits herein described can be used with or without a guide handle as will hereinafter be described. Further, it should be pointed out that is within the scope of the present invention to fabricate the milling bit or other cutting tool from metal as heretofore known, or to alternatively fabricate the milling bit or other cutting tool from a ceramic material. An advantage of a ceramic milling bit or cutting tool is that such resists wear and accordingly would be a non-disposable component of the present invention which would help to reduce the cost of the system of the present invention.

Three Dimensional Shaping

Figure 15A:
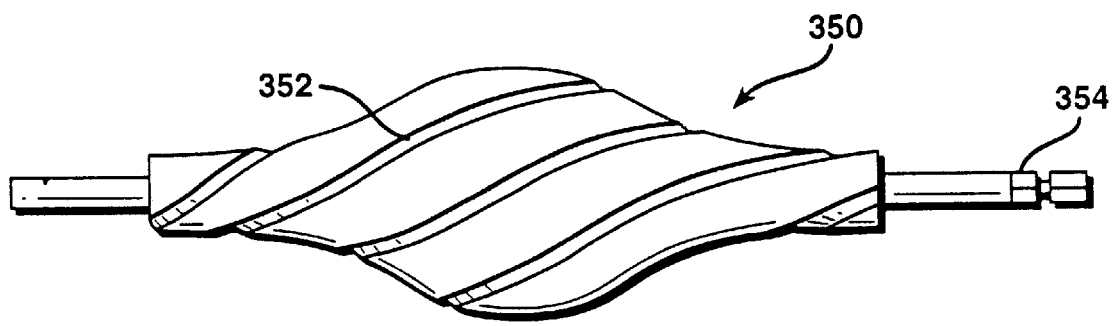
FIGS. 15A and B are front plan views of an embodiment of the cutting apparatus of the present invention for cutting a bone a in curvilinear cross-sectional plane.
Figure 15B:
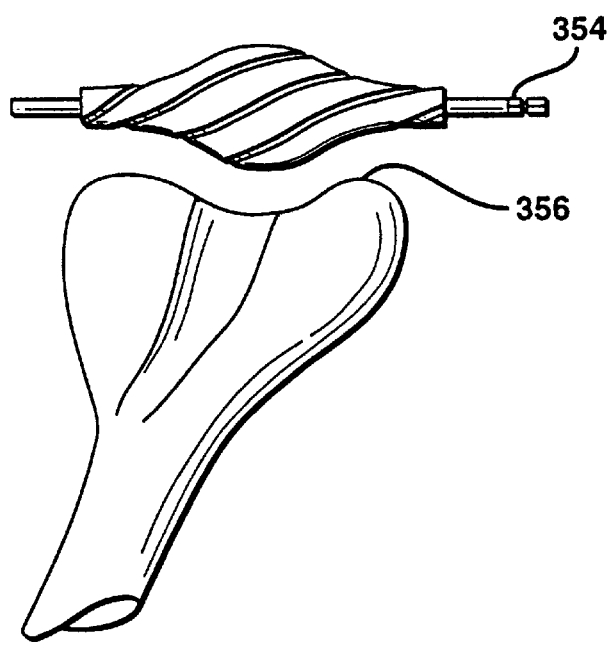

Initially, it should be noted that the term cutting profile the profile geometry of a mediolateral section taken normal to the cutting path through the bony surfaces created by cutting the bone. As shown in FIG. 15, in an alternate embodiment of the present invention, a milling apparatus having a three dimensional profile, or a form cutter, can be used to shape a bone in three dimensions. The curved profile milling bit 350, like the milling bits used in the previous embodiments of the present invention, includes cutting teeth 352 along the length thereof and spindles 354 at the ends thereof. This milling bit 330 can follow a pattern described by pattern plates and can be guided with a handle as will be hereinafter described.

Figure 17:
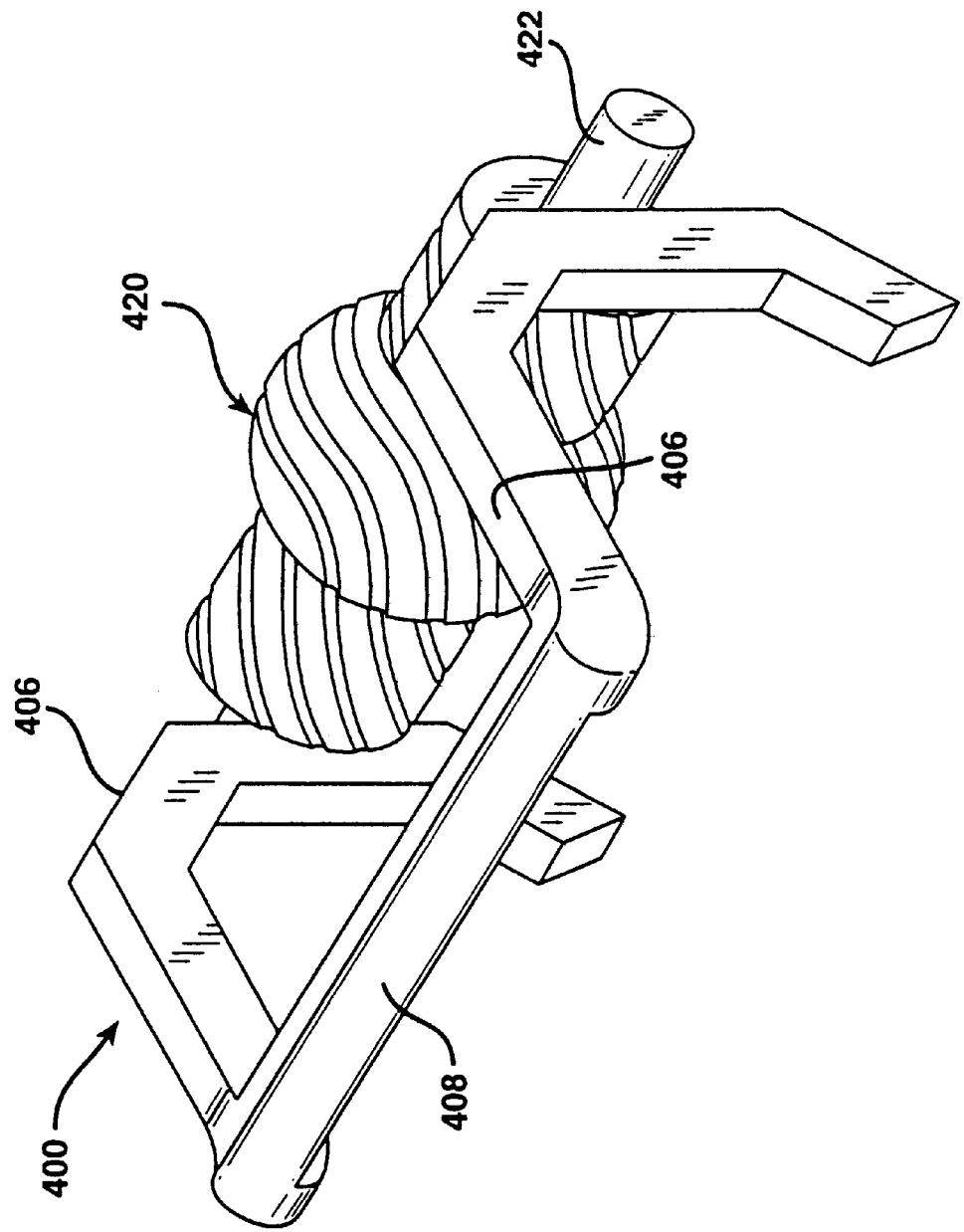
FIG. 17 is a perspective view of another embodiment of the pattern apparatus shown in FIG. 1, having a milling bit engaged therewith.

Importantly, by using a milling bit having a curved profile, one can cut a femur to resemble the natural shape of the femur, i.e. the resected femur would include condylar bulges and a central notch. This would reduce the amount of bony material that must be removed from the femur while maintaining the structural integrity of the femur. Of course, any prosthetic implant used for attachment to a femur resected by the curved profile milling bit would necessarily have an appropriately contoured inner fixation surface for mating with contoured surface of the femur. Additionally, it should be noted that the curved profile milling bit could have one or more curvilinear bulges along the length thereof as shown in FIG. 15, or alternatively, could have one or more bulges discretely formed along the length thereof as shown in FIG. 17.

Guide Handle

Figure 16:
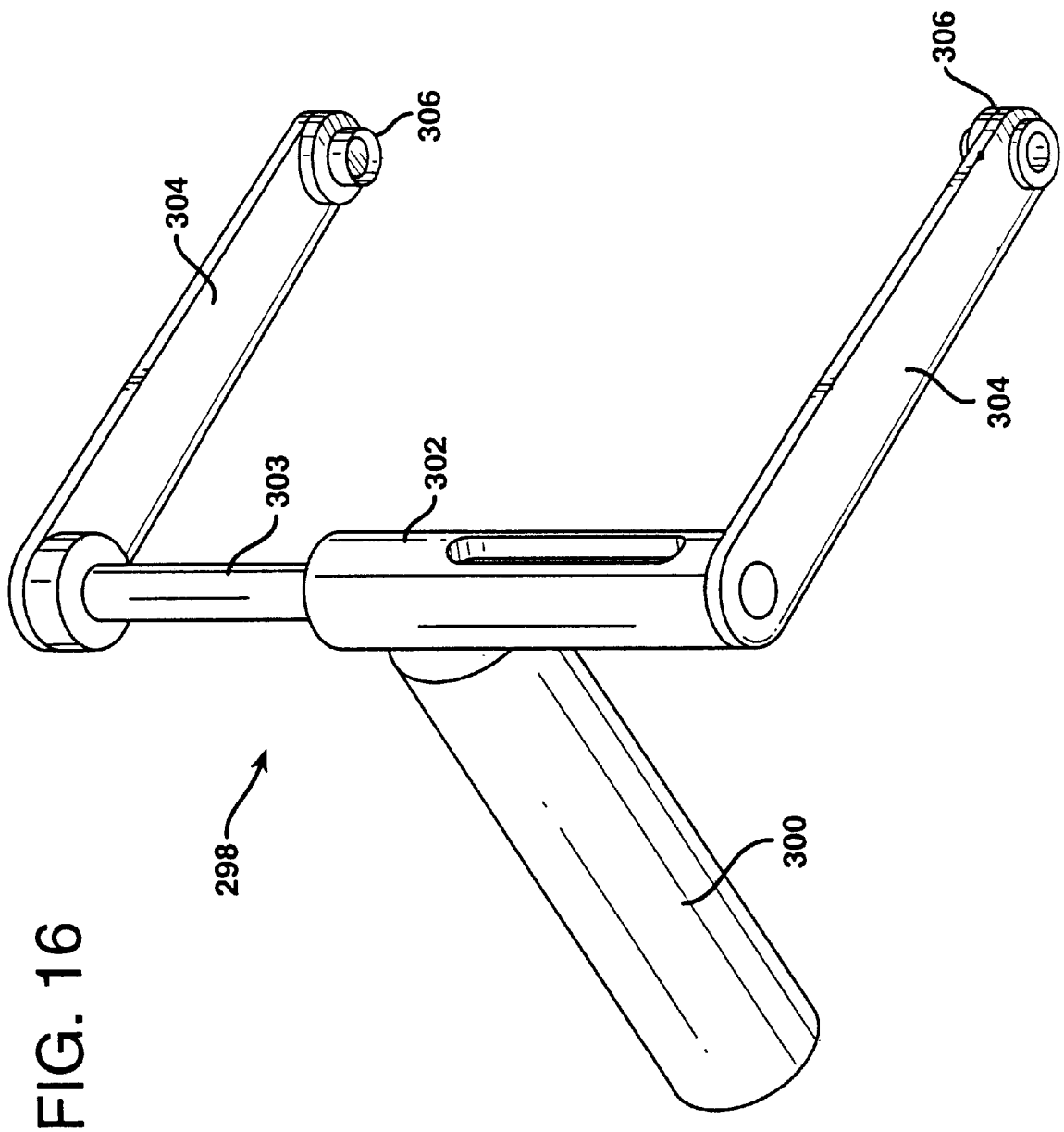
FIG. 16 is a perspective view of a handle for guiding a milling bit along a cutting path.

As shown in FIG. 16, a guide handle, generally indicated at 298 may be used to guide the milling bit along the cutting path of the pattern plate. The guide handle 298 comprises a grip portion 300 which is grasped by the user for manipulating the guide handle 298 and accordingly, the milling bit. The grip portion 300 is interconnected with a crossbar member 302 which includes a extension member 303 telescopically interconnected therewith. The crossbar member 302 and the extension member 303 may be positioned perpendicular with respect to grip portion. The extension member 303 is telescopically movable in and out of crossbar member 302. Means may be provided for locking the relative position of the extension with respect to the crossbar. Also, it should be noted that the grip portion may rigidly or pivotally interconnected with the crossbar as desired.

Extending from outer ends of the crossbar 302 and the extension member 303 are sidebars 304 in facing and parallel relationship. The sidebars 304 have two ends, the first of which are interconnected with the crossbar and the extension member, and the second of which are configured to receive and capture spindles or bushings of a milling bit in spindle bushings 306. The spindle bushings are positioned in facing relation and could include captured bushings. The captured bushings receive the spindles of a milling bit. The captured bushings are sized be received by the cutting path in the pattern plates and coact therewith to guide a milling bit therealong. Accordingly, after the pattern plate or plates are attached to a bone, the milling bit placed into the cutting path. Next a milling handle 298 is positioned such the spindle bushings are aligned with the spindles of the milling bit. Next, the extension is actuated to retract into the crossbar to move the spindle bushings onto the spindles of the milling bit where they are captured. Next, the spindle bushings are positioned within the cutting path of a pattern plate or plates. If necessary, the extension and cross bar can be locked down to lock the entire apparatus. Next, the milling bit is actuated and the grip portion of the handle is grasped and manipulated to move the milling bit along the cutting path to cut a bone.

Distally Positioned Pattern Plate

Figure 18:
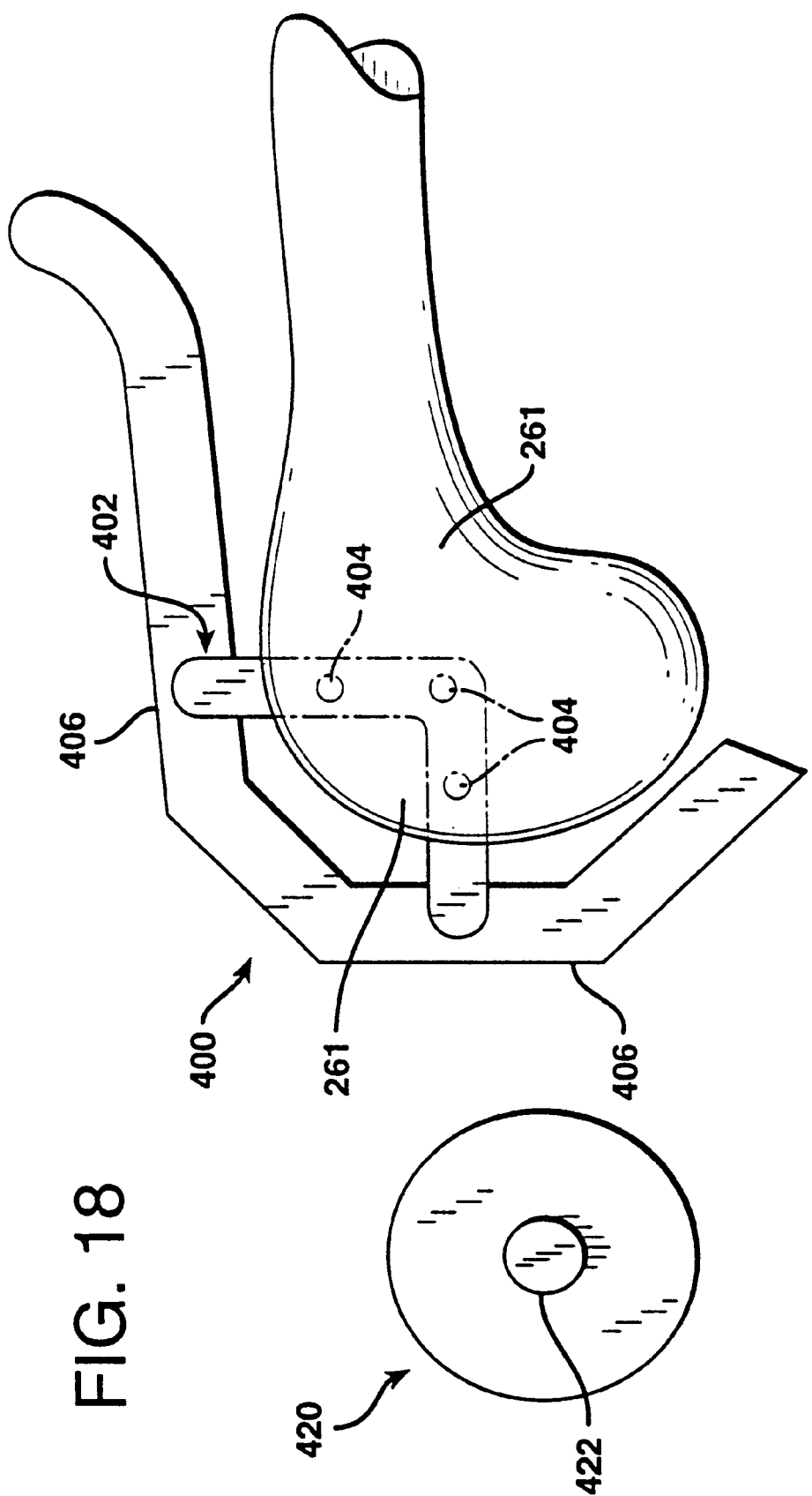
FIG. 18 is a side plan view of the pattern apparatus shown in FIG. 17 with the milling bit disengaged from the pattern apparatus.
Figure 19:
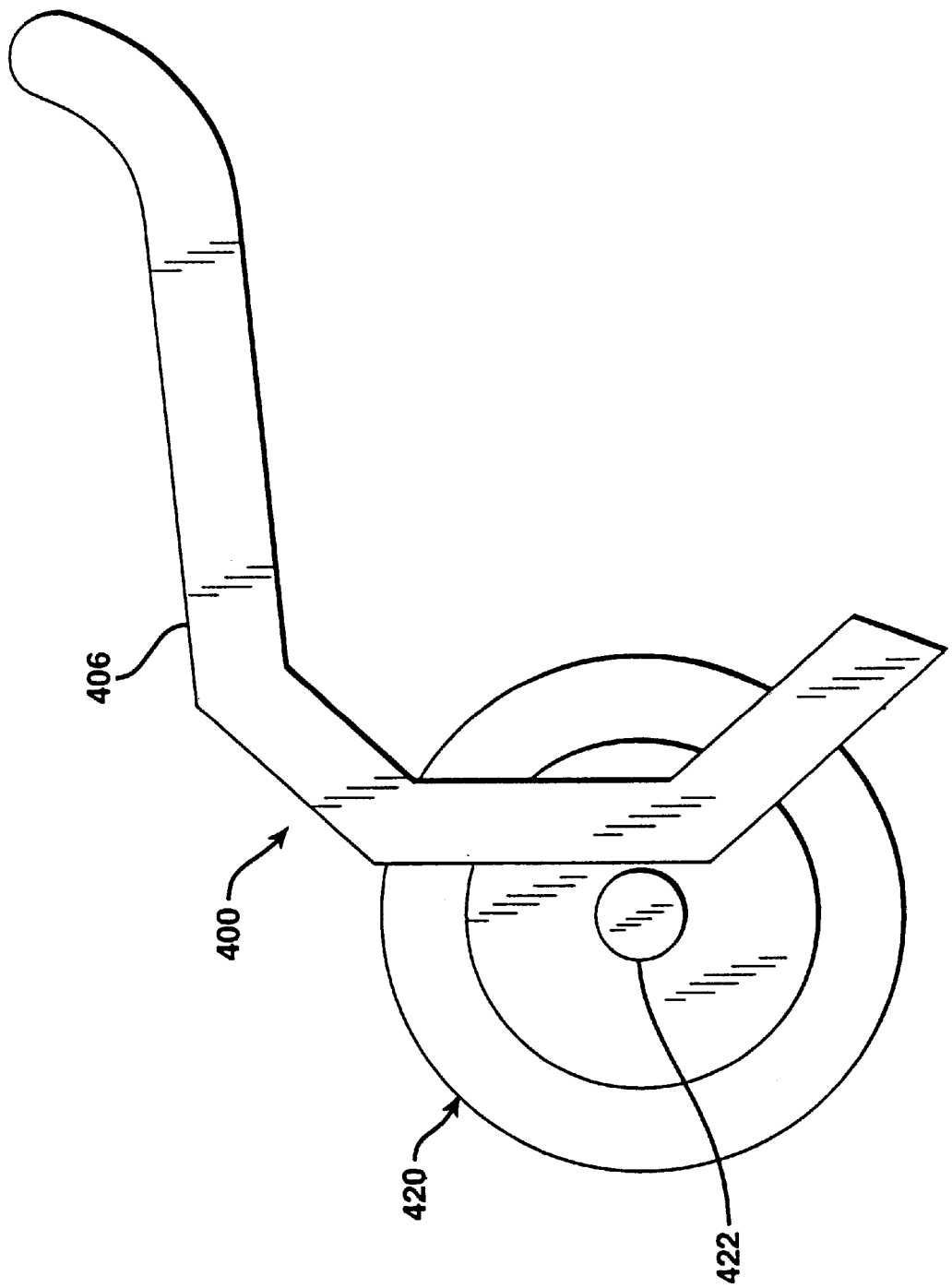
FIG. 19 is another side plan view of the pattern apparatus shown in FIG. 18 showing the milling bit engaged with the pattern apparatus.

As shown in FIGS. 17–19, in an alternate embodiment of the present invention for resecting a femur, the plate plates could take the form a rail assembly, generally indicated at 400, positioned distally of the distal femur 261. The plates could be affixed to the femur by fixation arms 402, attached at one or more points to the rail assembly 400, and including fixation apertures 404 for receiving fixation screws or other fixation means for attaching the fixation arms 402, and hence the rail assembly 400, to a distal femur 261. The rail assembly 400 includes one or more guide rails 406 which match the shape of the desired resection, though the rails may be larger or smaller depending on the dimensions of the milling apparatus used and the positioning of the assembly 400 with respect to the femur. In the case that the assembly 400 includes two guide rails 406, as shown, an end rail 408 may be used to interconnect such guide rails 406. The end rail 408 could be replaced by a connection means similar to the cross-bar apparatus 40 hereinbefore described. The rail assembly may be positioned on the distal femur in accordance with the teachings contained herein or in any other manner known in the art. After alignment according to any means disclosed herein or known or developed, and after fixation of the assembly to a femur, a milling bit 420 may be used to follow the guide rails 406 to resect the femur 261, the guide spindles 422, or bushings (not shown), of the milling bit 420, contacting and riding the guide rails 406. Importantly, the rail assembly 400 is attached to a femur and used in much the same way as the pattern plates previously described with the exception that rail assembly can be positioned substantially distal of the femur, thereby potentially requiring less exposure and possibly resulting in less interference for placement thereof. The rail assembly 400 could further include an upper retaining rail for forming a slot or cutting path for capturing the milling bit therein. Additionally, it should be noted that any milling bit described herein could be used with rail assembly 400 including a curved profile milling bit.

Curvilinear Implants

Figure 20:
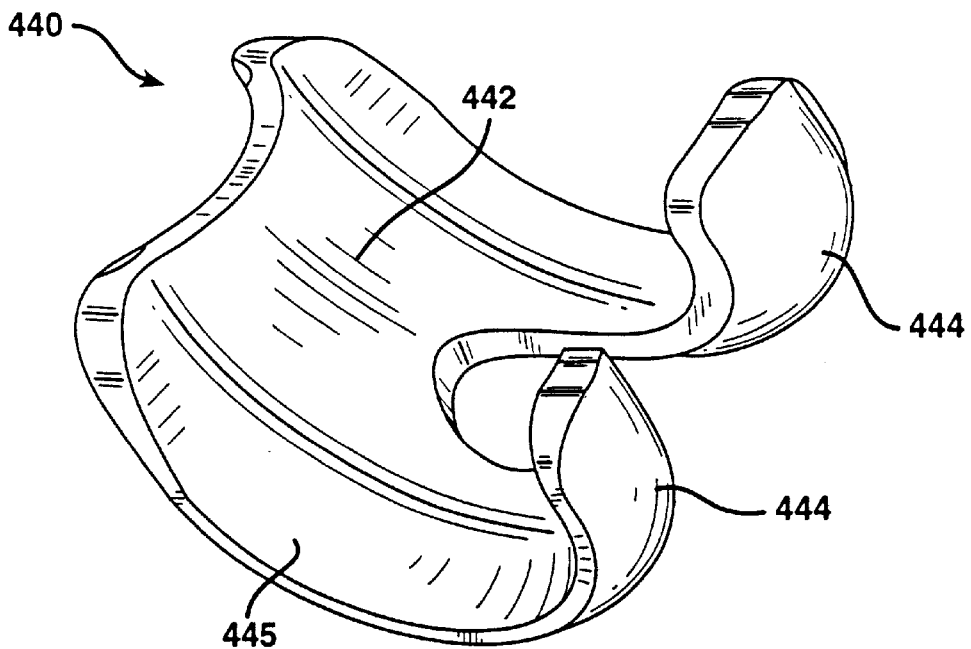
FIG. 20 is a perspective view of a femoral implant having a curved implant bearing surface.
Figure 21:
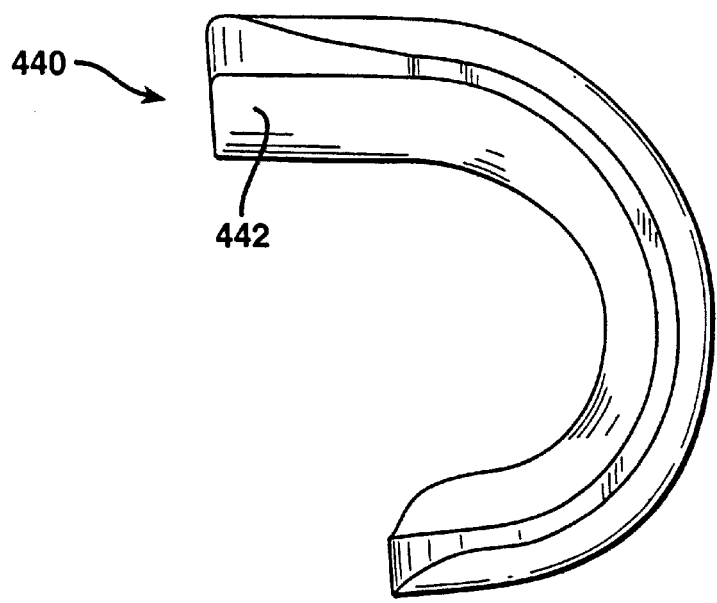
FIG. 21 is a side plan view of the femoral implant shown in FIG. 20.

As shown in FIGS. 20 and 21, an implant 440 may have curvilinear interior surfaces 442 as well as a more conventional curvilinear exterior surface. The particular example cited herein is a femoral implant used in total knee arthroplasty but the principles described herein may be applied to any application where foreign or indigenous material is affixed to an anatomic feature. The curvilinear bone surfaces necessary for proper fixation of such an implant may be generated through the use of the curvilinear milling or form cutter and the curvilinear cutting path means discussed herein. While it is possible to use multiple form cutters with differing geometries and therefore an implant with an internal geometry that varies along the cutting path from the anterior to the posterior of a femur, for the sake of intraoperative time savings a single form cutter is preferable.

The mediolateral cross-sectional internal geometry of such an implant, and therefore the necessary resected bony surfaces of the femur, are consistent about the cutting path in a single form cutter system. It should be noted that the implant may possess a notch between members 444 (posterior femoral implant condyles) in the areas approximately in between the distal and posterior femoral condylar areas to accommodate the posterior cruciate ligament and other factors. Because of the notch between the posterior femoral condyles it may not be necessary for the form cutter to cut any material in the notch. It may be desirable to provide outer flat surfaces 445 with an adjoining curvilinear surface 442 positioned therebetween. Other combinations of flat or curvilinear surfaces are also within the scope of the present invention.

Figure 29:
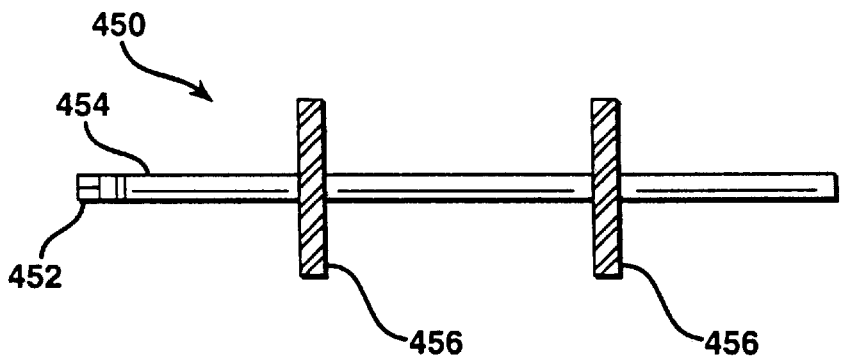
FIG. 29 is front plan view of another cutting apparatus for use in connection with the present invention.

Additionally, it may be advantageous to utilize a secondary form cutter as shown in FIG. 29 for use in creating a slet or slots in or near the distal area of the femur after it has been resected. Such a secondary cutter 450 would include engagement means 452 for engagement with driving means, and a shaft 454 carrying cutters 456 for cutting slots into the femur through one or more of the resected surfaces thereof. Through the inclusion of an additional or adjunct cutting path in the pattern means, it would be advantageous to utilize the form cutter to create the aforementioned slots to accommodate the fixation fins which may be molded as an integral part of the interior surface of the implant. These fins would provide mediolateral fixation stability in addition to that provided by the trochlear groove geometry of the implant. Further, the fins also provide for additional surface area for bony contact and ingrowth to increase implant fixation both in cemented and cementless total knee arthroplasty.

There are numerous advantages to the femoral component herein described. Foremost, it will allow for the thinnest implant cross-section possible (perhaps 3 mm to 6 mm in thickness) and therefore necessitate the removal of the least amount of viable osseous tissue. This is especially critical in situations where the probability of revision surgery is high and the amount of viable bone available for revision implant fixation and apposition is a significant factor in the viability of the revision procedure. Since the form cutter configuration allows for similar amounts of tissue to be removed from the trochlear groove, the bony prominences surrounding the trochlear groove, the femoral condyles, and the other articular surfaces of the femur, the external geometry of the femoral implant can be optimized for patellofemoral articulation as well as tibiofemoral articulation. In essence, the kinematics of the artificial joint could be made to be as close as possible to that of a healthy, natural knee joint. In addition, the curvilinear geometry of the implant dramatically decreases the stress risers inherent in conventional rectilinear femoral implants and allows for a thinner cross-sectional geometry while potentially increasing the resistance of the implant to mechanical failure under fatigue or impact loading. Conversely, the curvilinear geometry of the implant may also allow for an advantageous reduction in the flexural rigidity of the implant which may result in avoidance of the "stress-shielding" inherent in rigid implant designs. Stress shielding being a phenomenon that may occur when living bony tissue is prevented from experiencing the stresses necessary to stimulate its growth by the presence of a stiff implant. This phenomenon is analogous to the atrophy of muscle tissue when the muscle is not used, i.e. when a cast is placed on a person's arm the muscles in that arm gradually weaken for lack of use.

Additionally, the curvilinear implant design may allow for the use of a ceramic material in its construction. Since ceramics are generally relatively weak in tension, existing ceramic implant designs contain very thick cross-sections which require a great deal of bony material removal to allow for proper implantation. Utilization of ceramics in the curvilinear implant will not only allow for the superior surface properties of ceramic, but also avoid the excessively thick cross-sections currently required for the use of the material.

This could result in a less expensive femoral implant because of the reduced amount of material needed for the implant, as well as an improved, more natural, and even stronger knee replacement. It may desirable to vary the cross-section of the implant 440 to assist in seating the implant and to increase the strength and fit of the implant. The implants of the present invention having curvilinear implant surfaces could be fabricated of metal, plastic, or ceramic or any other material. Further, the thickness of the implants and the material required to fabricate the implant could be reduced as the implants are adapted to increasingly curvilinear surfaces. Also, it should be pointed out the such implants with curvilinear implant surfaces require less bone to be removed to obtain a fit between the implant and the bone. Finally, it should be noted that curvilinear milling bits hereinbefore described would work well for preparing a bone to receive an implant with curvilinear interior implant surface.

Patella Shaping

The apparatus for preparing a patella, as shown in FIGS. 22–24, comprises a plier-like patella resection apparatus generally indicated at 500. The patella resection apparatus 500 includes grip handles 502 for manipulating the apparatus, cross-over members 504 pivotally interconnected with each other by pin 506, and patella clamp members 508 extending from the cross-over members in parallel and facing relation. The patella clamp members 508 have beveled edges 510 for contacting and supporting a patella along the outer edges thereof. Guide member structures 512 are mounted on each of the patella clamp members 508 to form a retainer for a cutting means to follow a cutting path defined by the upper surface of the clamp members. Bushings 514 are captured in within the retainer and the cutting path for receiving a cutting means 516 and guiding the cutting means 516 along the cutting path.

In preparing the patella, the pattern device may be an integral part of the positioning apparatus which is oriented and located by referencing the geometry of the patella itself as well as the structures of the patellofemoral mechanism to determine the location and orientation of a predominantly planar resection. The cutting device may then be employed to perform the resection of the patella by traversing the path dictated by the pattern device, thus dictating the final location and orientation of the patella prosthesis.

Bone Substitution and Shaping

Figure 25:
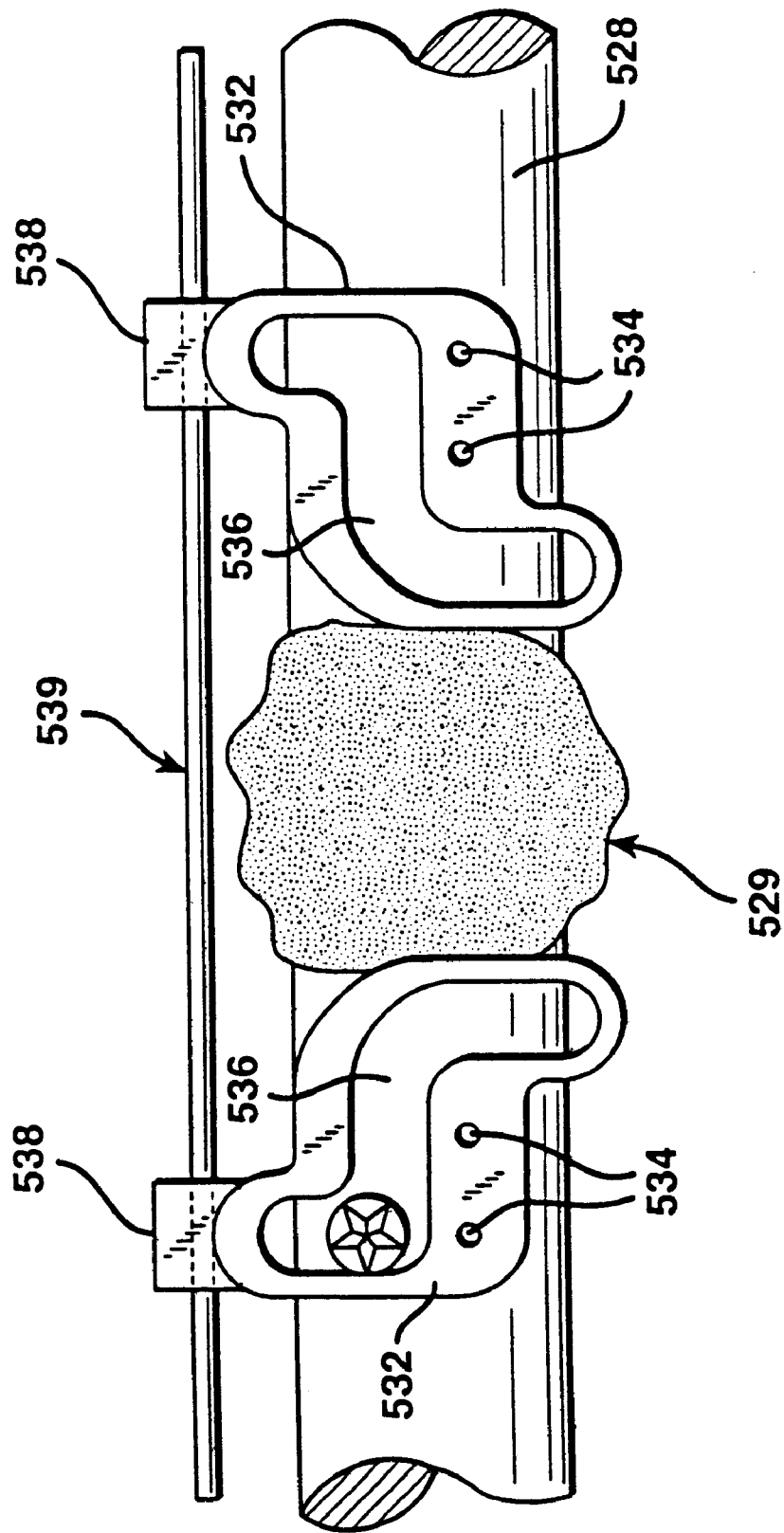
FIG. 25 is a perspective view of another embodiment of the pattern apparatus of the present invention for cutting a bone.

Referring now to FIG. 25, another embodiment of the pattern apparatus of the present invention for cutting bone is shown. This embodiment of the invention includes pattern plates 532 having cutting paths 536 described therein. The pattern plates 532 may be positioned on a bone 528 having a tumor or other pathology 529 associated therewith. The pattern plates 532 may be interconnected by cross bars 538 with opposing pattern plates (not shown) positioned on the opposite side of the bone 528. Further, each set of pattern plates 532 could be interconnected by means of positioning rod 539 extending between the cross bars 538 to maintain the relative location and orientation between the sets of pattern plates 532. The pattern plates can be positioned along the bone in accordance with what is known in the art, disclosed herein or hereafter developed. After the pattern plates are properly positioned, they can be affixed to the bone 528 with fixation means extending through fixation apertures 534. After the pattern plates are properly located and affixed to the bone, cutting can commence by traversing a cutting means along the cutting paths 536 of the pattern plates 532. By this step, the tumor or other pathology 529 can be cut from the bone 528 and a bone graft or other surgical procedure can be implemented to repair and/or replace the bone that has been cut. The benefits of cutting a bone with the pattern plates of the present invention include providing smooth and even cuts to the bone to facilitate fixation of bone grafts or other means for repairing and/or replacing bone. Further, the same pattern plates can be used to cut another identical sized and shaped bone for grafting to the first bone to replace the cut away bone.

Alternate Positioning and Alignment Guide

Figure 26:
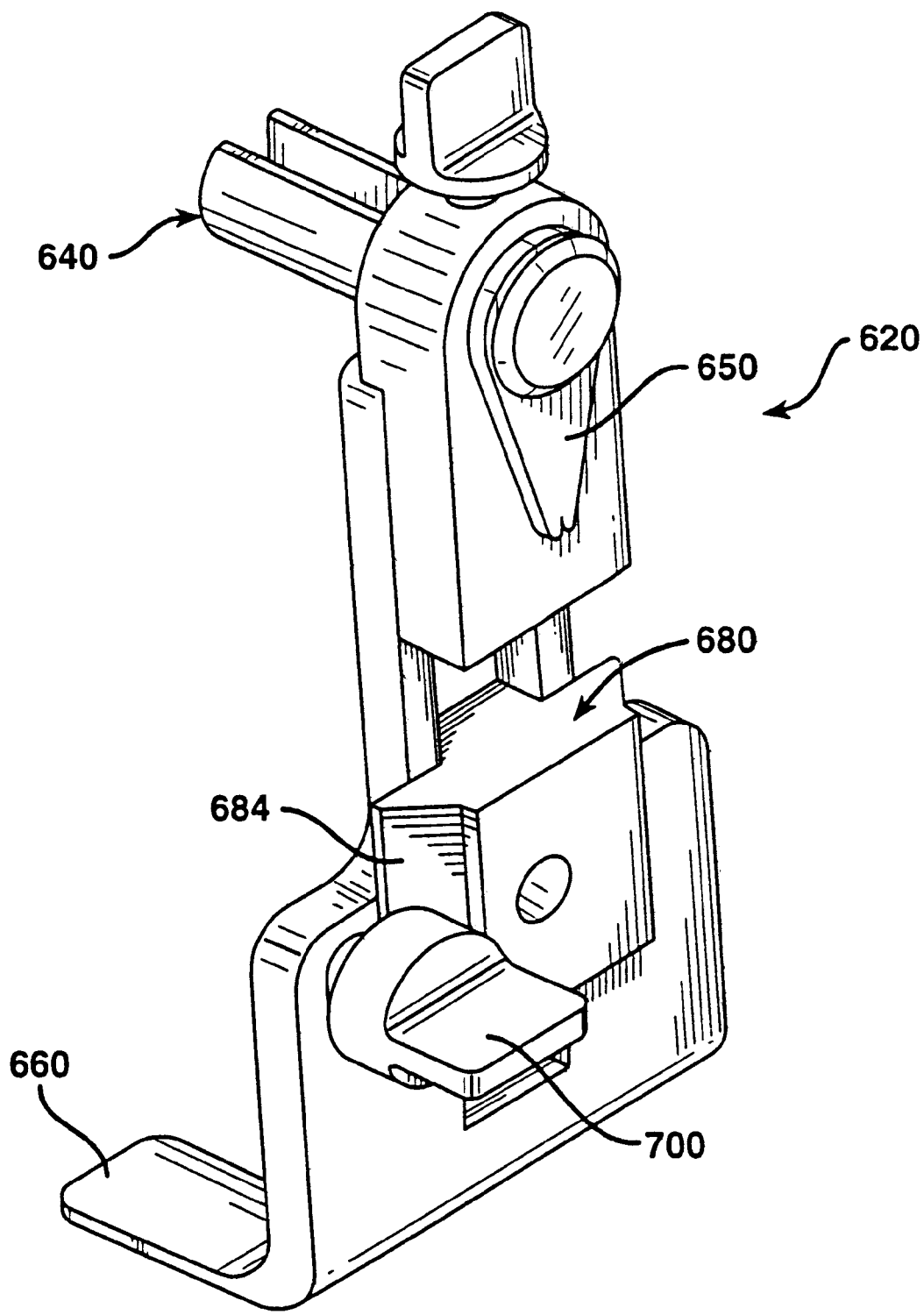
FIG. 26 is a perspective view of another embodiment of the alignment apparatus shown in FIG. 6.

An alternate positioning and alignment guide is generally indicated at 620 in FIG. 26. The positioning body 620 comprises a cross bar linkage 640 and an alignment indicator 650 at an upper end thereof for interconnecting with a cross bar to align pattern plates interconnected with such cross bar. The positioning body 620 also includes an alignment block 680 for interconnecting with an intramedullary rod in much the same manner as the IM rod guide block shown in FIG. 10. The alignment block 680 is vertically movable along the positioning body 620 and can be locked into a desired position by means of lock screw 700 which bears against a flange 684 of the alignment block 680. The positioning body 620 further includes skids 660 for contacting the posterior surface of the distal femoral condyles for referencing same.

Unicondylar and/or Single Pattern Plate Support

Figure 27:
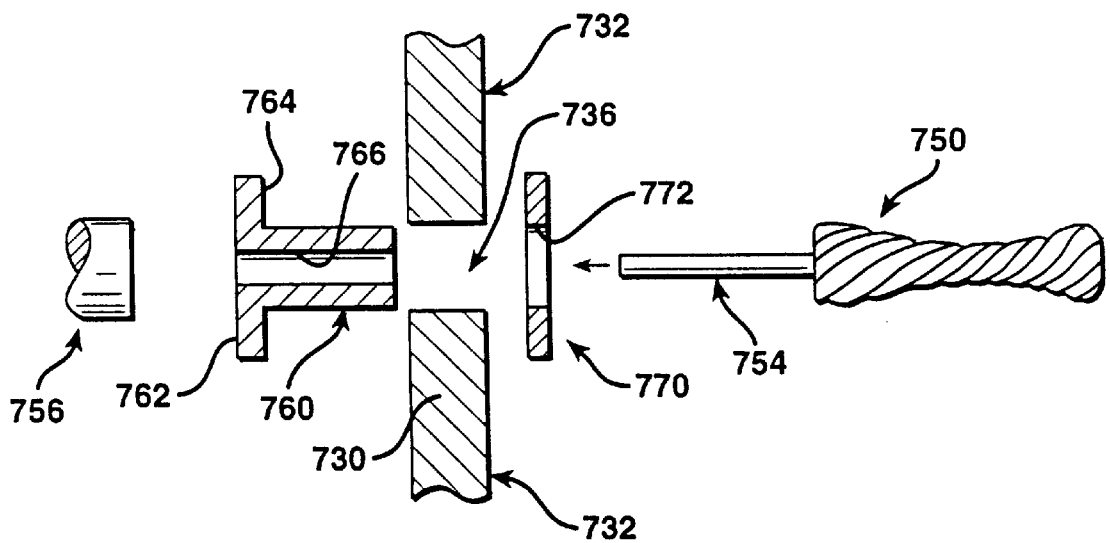
FIG. 27 is a partially exploded side plan view of another embodiment of the pattern apparatus of the present invention for cutting a bone.
Figure 28:
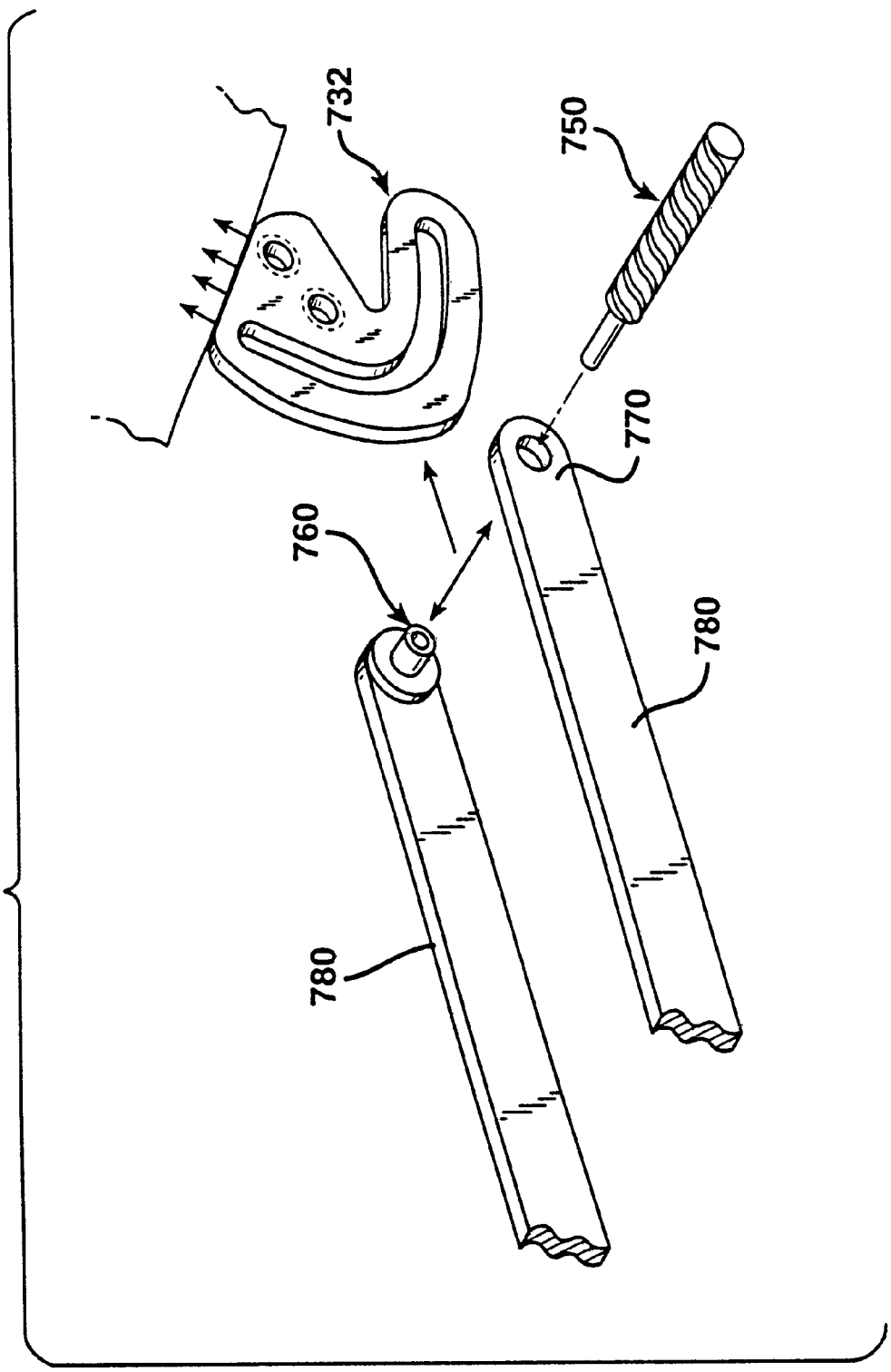
FIG. 28 is a partially exploded perspective view of the interconnection of a handle with milling bit for use in connection with pattern plate shown in FIG. 27.

As shown in FIGS. 27 and 28, one pattern plate of the present invention can be used by itself to guide a cutting means along a cutting path to cut a bone. Such an application is particularly useful for unicondylar resecting of a femur. Use of a single pattern plate 732 is facilitated by bushing 760 having an outer flange 762 with a bearing surface 764 and an internal bore 766 sized to receive a spindle 754 of a cutting tool therein. The bushing 760 is sized to fit into the cutting path 736 of the pattern plate 732, the bearing surface 764 of the flange 762 contacting the side of the pattern plate 732. Washer 770 includes a central bore 772 sized to received the far end of the bushing 760 extending past the pattern plate 732, the washer bearing against the side of the pattern plate 732 opposite the side that the bearing surface 764 of the flange 762 of the bushing 760 bears against. Thus the washer and the bushing coact to form a stable link with a pattern plate. As shown in FIG. 28, this link can be fortified by means of bearing arms 780 interconnected with the bushing and the washer, or formed integrally as part thereof, which by pressure means are forced together to retain the bushing within the cutting path of the pattern plate. After the bushing is captured within the cutting path, the spindle of the cutting means can be inserted through the bushing and interconnected with means 756 for driving the cutting means. Alternatively, it should be pointed out that when using a single pattern plate to cut a bone, it may be desirable to support the cutting means at the pattern plate and also at the other end thereof. One could effect such desired support at the other end of the cutting means by a brace or other linkage interconnecting the other end of the cutting means with a secondary support or anchor means positioned on the opposite side of the bone or at another location.

Revisions

Conventional revisions require removal of the old implant and the referencing of uncertain landmarks. Revisions by means of the present invention allow for reference of the implant while it is still on the bone. One can obtain varus/valgus referencing, distal resection depth, posterior resection depth and rotational alignment by referencing the geometry of the implant with the alignment guide. An extramedullary alignment rod can be used to facilitate flexion/extension alignment. The fixation screws can then be advanced to touch the bone and mark their location by passing standard drill bits or pins through the cannulations in the fixation screws and into the bone. Then, the pattern and guide device are removed, the old implant removed, and the pattern device repositioned by means of the marked location of the fixation screws and then fixed into place. Accordingly, the cuts for the new implant, and thus the new implant itself, are located and orientated based off of the old implant. This results in increased precision and awareness of the final implant location and orientation as well as potential intraoperative time savings.

Modifications of the foregoing may be made without departing from the spirit and scope of the invention. What is desired to be protected by Letters Patents is set forth in the appended claims.

What is claimed is:

1. A method for resecting a patella comprising the steps of:

positioning pattern means along at least one side of a patella, the pattern means including a cutting path having a guide surface;

affixing the pattern means to a patella;

interconnecting a cutting means with the pattern means, the cutting means comprising a cylindrical milling bit; and traversing the cutting means along the cutting path of the pattern means by manipulating the cutting means to continuously traverse the cutting path to resect a patella.

2. The method of claim 1 wherein the step of traversing the cutting means along the cutting path comprises the steps of grasping a handle interconnected with the cutting means and guiding the cutting means along the cutting path by manipulating the handle.

3. The method of claim 1 further comprising positioning pattern means along opposite sides of a patella.

4. The method of claim 3 wherein the pattern means are formed on gripping surfaces of plier means and the step of affixing the pattern means to a patella comprises squeezing grip portions of the plier means.

5. The method of claim 3 wherein the step of positioning the pattern means along a patella further comprises contacting a depth indicator against a patella.

6. A guide handle for guiding a milling bit to cut a bone, the guide handle comprising:

grip means for grasping the handle;

crossbar means interconnected with the handle;

sidebar means extending in facing relation from the crossbar means; and retention means positioned on the sidebar means for receiving and retaining a milling bit.

7. The guide handle of claim 6 wherein the retention means further includes bushing means for positioning about spindles of a milling bit.

8. The guide handle of claim 7 wherein the bushing means are sized to be received in within a cutting path of a pattern plate.

9. The guide handle of claim 6 wherein the crossbar is adjustable in size.

10. The guide handle of claim 9 further including lock means for locking the size of the crossbar.

11. A method of using a guide handle to guide a milling bit to cut bone comprising the steps of:

attaching one or more pattern plates having a cutting path to a bone to be cut;

inserting a milling bit into the cutting path;

positioning a guide handle into alignment with the milling bit;

retracting a crossbar of the guide handle to move sidebars of the guide handle against the ends of the milling bit to position the ends of the milling bit within bushings on the sidebars;

positioning the bushings within the cutting path;

locking the crossbar;

actuating the milling bit; and using a handle on the guide handle to manipulate the milling bit along the cutting path to cut a bone.

12. An apparatus for resecting a patella comprising:

grip handles for manipulating the apparatus;

cross-over members pivotally interconnected;

patella clamp members extending from the cross-over members in facing relation;

guide means associated with the clamp members for guiding a cutting means along a cutting path; and bushings captured within the guide means for receiving the cutting the means and guiding the cutting means along the cutting path.

13. The apparatus of claim 12 further including beveled edge members on the clamp members for contacting and supporting a patella.

14. The apparatus of claim 13 further comprising a depth indicator for positioning the device with respect to a patella.

15. The apparatus of claim 13 further comprising pin means for interconnecting the cross-over members.

* * * * *